US009375255B2

(12) United States Patent
Houser et al.

(10) Patent No.: US 9,375,255 B2
(45) Date of Patent: Jun. 28, 2016

(54) SURGICAL INSTRUMENT HANDPIECE WITH RESILIENTLY BIASED COUPLING TO MODULAR SHAFT AND END EFFECTOR

(75) Inventors: Kevin L. Houser, Springboro, OH (US); Barry C. Worrell, Centerville, OH (US); Stephen J. Balek, Springboro, OH (US); Galen C. Robertson, Durham, NC (US); Frederick E. Shelton, IV, Hillsboro, OH (US); Richard W. Timm, Cincinnati, OH (US); Kyle P. Moore, Mason, OH (US); Gregory W. Johnson, Cincinnati, OH (US); John B. Schulte, West Chester, OH (US); Daniel J. Mumaw, Johannesburg (SA)

(73) Assignee: Ethicon Endo-Surgery, LLC, Los Frailes Industrial Park, Guaynabo, PR (US)

( * ) Notice: Subject to any disclaimer, the term of this patent is extended or adjusted under 35 U.S.C. 154(b) by 806 days.

(21) Appl. No.: 13/271,352

(22) Filed: Oct. 12, 2011

(65) Prior Publication Data
US 2012/0116363 A1 May 10, 2012

Related U.S. Application Data

(60) Provisional application No. 61/410,603, filed on Nov. 5, 2010, provisional application No. 61/487,846, filed on May 19, 2011.

(51) Int. Cl.
*A61B 17/00* (2006.01)
*A61B 18/14* (2006.01)
(Continued)

(52) U.S. Cl.
CPC ....... *A61B 18/1442* (2013.01); *A61B 17/00234* (2013.01); *A61B 17/2812* (2013.01);
(Continued)

(58) Field of Classification Search
CPC .............................................. A61B 2017/2931
USPC ............................................................. 606/1
See application file for complete search history.

(56) References Cited

U.S. PATENT DOCUMENTS 1,754,806 A 4/1930 Stevenson
3,297,192 A 1/1967 Swett
(Continued)

FOREIGN PATENT DOCUMENTS

DE 102008051866 10/2010
DE 102009013034 10/2010
(Continued)

OTHER PUBLICATIONS

U.S. Appl. No. 13/151,471, filed Jun. 2, 2011, Stulen.
(Continued)

*Primary Examiner* — Aaron Roane

(57) ABSTRACT

An ultrasonic surgical instrument includes a reusable handle assembly and a removable and disposable transmission assembly. The handle assembly includes a trigger, a housing having a distal aperture formed in a distal end of the housing, a button disposed on a top surface of the housing, and a biasing member in communication with the button. The transmission assembly includes a proximal shaft, a rotator knob having a coupling feature, a distal shaft assembly extending distally from the proximal shaft, and an end effector at the distal end of the distal shaft assembly. The biasing member of the handle assembly is adjustably coupled to the coupling feature of the transmission assembly. Another version includes a movable yoke configured to engage an inner tube of the transmission assembly. Yet another version includes a waveguide of the transmission assembly non-threadably coupled to a transducer via a biasing force.

14 Claims, 11 Drawing Sheets

(51) Int. Cl.

| | | |
|---|---|---|
| *A61B 17/32* | (2006.01) | |
| *A61B 18/00* | (2006.01) | |
| *A61B 18/04* | (2006.01) | |
| *H02J 7/00* | (2006.01) | |
| *A61B 17/28* | (2006.01) | |
| *H01M 2/26* | (2006.01) | |
| *H01M 2/10* | (2006.01) | |
| *A61B 18/12* | (2006.01) | |
| *A61B 19/00* | (2006.01) | |
| *A61B 17/064* | (2006.01) | |
| *A61B 17/285* | (2006.01) | |
| *A61B 17/29* | (2006.01) | |

(52) U.S. Cl.
CPC . *A61B17/320068* (2013.01); *A61B 17/320092* (2013.01); *A61B 18/00* (2013.01); *A61B 18/04* (2013.01); *A61B 18/12* (2013.01); *A61B 18/14* (2013.01); *A61B 18/1445* (2013.01); *H02J 7/0045* (2013.01); *A61B 17/064* (2013.01); *A61B 17/285* (2013.01); *A61B 18/1206* (2013.01); *A61B 18/1233* (2013.01); *A61B 19/38* (2013.01); *A61B 19/56* (2013.01); *A61B 2017/0046* (2013.01); *A61B 2017/00084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2018/0019* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2019/4815* (2013.01); *A61B 2019/4868* (2013.01); *A61B 2019/4873* (2013.01); *H01M 2/10* (2013.01); *H01M 2/26* (2013.01); *Y10T 29/49005* (2015.01); *Y10T 29/49895* (2015.01); *Y10T 29/53913* (2015.01)

(56) References Cited

U.S. PATENT DOCUMENTS

| | | | |
|---|---|---|---|
| 3,419,198 | A | 12/1968 | Pettersen |
| 3,619,671 | A | 11/1971 | Shoh |
| 4,034,762 | A | 7/1977 | Cosens et al. |
| 4,057,220 | A | 11/1977 | Kudlacek |
| 4,535,773 | A | 8/1985 | Yoon |
| 4,641,076 | A | 2/1987 | Linden et al. |
| 4,662,068 | A | 5/1987 | Polonsky |
| 4,666,037 | A | 5/1987 | Weissman |
| 4,685,459 | A | 8/1987 | Koch et al. |
| 4,717,018 | A | 1/1988 | Sacherer et al. |
| 4,717,050 | A | 1/1988 | Wright |
| 4,721,097 | A | 1/1988 | D'Amelio |
| 4,768,969 | A | 9/1988 | Bauer et al. |
| 4,800,878 | A | 1/1989 | Cartmell |
| 4,844,259 | A | 7/1989 | Glowczewskie, Jr. et al. |
| 4,878,493 | A | 11/1989 | Pasternak et al. |
| 5,071,417 | A | 12/1991 | Sinofsky |
| 5,107,155 | A | 4/1992 | Yamaguchi |
| 5,144,771 | A | 9/1992 | Miwa |
| 5,169,733 | A | 12/1992 | Savovic et al. |
| 5,176,677 | A | 1/1993 | Wuchinich |
| 5,246,109 | A | 9/1993 | Markle et al. |
| 5,273,177 | A | 12/1993 | Campbell |
| 5,277,694 | A | 1/1994 | Leysieffer et al. |
| 5,308,358 | A | 5/1994 | Bond et al. |
| 5,322,055 | A | 6/1994 | Davison |
| 5,339,799 | A | 8/1994 | Kami et al. |
| 5,358,508 | A | 10/1994 | Cobb et al. |
| 5,361,902 | A | 11/1994 | Abidin et al. |
| 5,429,229 | A | 7/1995 | Chester et al. |
| 5,449,370 | A | 9/1995 | Vaitekunas |
| 5,454,378 | A | 10/1995 | Palmer et al. |
| 5,501,607 | A | 3/1996 | Yoshioka et al. |
| 5,507,297 | A * | 4/1996 | Slater et al. .................. 600/564 |
| 5,561,881 | A | 10/1996 | Klinger et al. |
| 5,578,052 | A | 11/1996 | Koros et al. |
| 5,580,258 | A | 12/1996 | Wakata |
| 5,582,617 | A | 12/1996 | Klieman et al. |
| 5,590,778 | A | 1/1997 | Dutchik |
| 5,592,065 | A | 1/1997 | Oglesbee et al. |
| 5,599,350 | A | 2/1997 | Schulze et al. |
| 5,630,420 | A | 5/1997 | Vaitekunas |
| 5,630,456 | A | 5/1997 | Hugo et al. |
| 5,690,222 | A | 11/1997 | Peters |
| 5,707,369 | A | 1/1998 | Vaitekunas et al. |
| 5,741,305 | A | 4/1998 | Vincent et al. |
| 5,776,155 | A | 7/1998 | Beaupre et al. |
| 5,800,336 | A | 9/1998 | Ball et al. |
| 5,817,128 | A | 10/1998 | Storz |
| 5,868,244 | A | 2/1999 | Ivanov et al. |
| 5,871,493 | A | 2/1999 | Sjostrom et al. |
| 5,873,873 | A | 2/1999 | Smith et al. |
| 5,882,310 | A | 3/1999 | Marian, Jr. |
| 5,893,835 | A | 4/1999 | Witt et al. |
| 5,893,874 | A | 4/1999 | Bourque et al. |
| 5,935,144 | A | 8/1999 | Estabrook |
| 5,938,633 | A | 8/1999 | Beaupre |
| 5,944,737 | A | 8/1999 | Tsonton et al. |
| 5,951,575 | A | 9/1999 | Bolduc et al. |
| 5,980,510 | A | 11/1999 | Tsonton et al. |
| 5,997,531 | A | 12/1999 | Loeb et al. |
| 6,018,227 | A | 1/2000 | Kumar et al. |
| 6,051,010 | A | 4/2000 | DiMatteo et al. |
| 6,056,735 | A | 5/2000 | Okada et al. |
| 6,063,098 | A | 5/2000 | Houser et al. |
| 6,066,151 | A | 5/2000 | Miyawaki et al. |
| 6,083,191 | A | 7/2000 | Rose |
| 6,083,223 | A | 7/2000 | Baker |
| 6,099,537 | A | 8/2000 | Sugai et al. |
| 6,113,593 | A | 9/2000 | Tu et al. |
| 6,123,702 | A | 9/2000 | Swanson et al. |
| 6,165,191 | A | 12/2000 | Shibata et al. |
| 6,190,386 | B1 | 2/2001 | Rydell |
| 6,204,592 | B1 | 3/2001 | Hur |
| 6,214,023 | B1 | 4/2001 | Whipple et al. |
| 6,246,896 | B1 | 6/2001 | Dumoulin et al. |
| 6,248,238 | B1 | 6/2001 | Burtin et al. |
| 6,287,304 | B1 | 9/2001 | Eggers et al. |
| 6,325,811 | B1 | 12/2001 | Messerly |
| 6,339,368 | B1 | 1/2002 | Leith |
| 6,398,755 | B1 | 6/2002 | Belef et al. |
| 6,409,742 | B1 | 6/2002 | Fulton, III et al. |
| 6,500,176 | B1 | 12/2002 | Truckai et al. |
| 6,500,188 | B2 | 12/2002 | Harper et al. |
| 6,512,667 | B2 | 1/2003 | Shiue et al. |
| 6,514,267 | B2 | 2/2003 | Jewett |
| 6,520,185 | B1 | 2/2003 | Bommannan et al. |
| 6,561,983 | B2 | 5/2003 | Cronin et al. |
| 6,562,032 | B1 | 5/2003 | Ellman et al. |
| 6,609,414 | B2 | 8/2003 | Mayer et al. |
| 6,622,731 | B2 | 9/2003 | Daniel et al. |
| 6,623,500 | B1 | 9/2003 | Cook et al. |
| 6,626,901 | B1 | 9/2003 | Treat et al. |
| 6,647,281 | B2 | 11/2003 | Morency |
| 6,650,091 | B1 | 11/2003 | Shiue et al. |
| 6,650,975 | B2 | 11/2003 | Ruffner |
| 6,656,177 | B2 | 12/2003 | Truckai et al. |
| 6,658,301 | B2 | 12/2003 | Loeb et al. |
| 6,666,875 | B1 | 12/2003 | Sakurai et al. |
| 6,706,038 | B2 | 3/2004 | Francischelli et al. |
| 6,717,193 | B2 | 4/2004 | Olewine et al. |
| 6,730,042 | B2 | 5/2004 | Fulton et al. |
| 6,753,673 | B2 | 6/2004 | Shiue et al. |
| 6,758,855 | B2 | 7/2004 | Fulton, III et al. |

(56) References Cited

U.S. PATENT DOCUMENTS

| | | |
|---|---|---|
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,836,097 B2 | 12/2004 | Turner et al. |
| 6,838,862 B2 | 1/2005 | Luu |
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckal et al. |
| 7,364,061 B2 | 4/2008 | Swayze et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,573,151 B2 | 8/2009 | Acena et al. |
| 7,583,564 B2 | 9/2009 | Kitahara et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,717,312 B2 | 5/2010 | Beetel |
| 7,721,936 B2 | 5/2010 | Shalton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,918,848 B2 | 4/2011 | Lau et al. |
| 7,922,063 B2 | 4/2011 | Zemlok et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,608 B2 | 8/2012 | Omori et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,882 B2 | 10/2012 | Danek et al. |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,551,088 B2 | 10/2013 | Falkenstein et al. |
| 8,564,242 B2 | 10/2013 | Hansford et al. |
| 8,573,461 B2 | 11/2013 | Shelton et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 9,044,261 B2 | 6/2015 | Houser |
| 2001/0032666 A1 | 10/2001 | Jenson et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton et al. |
| 2005/0171522 A1 | 8/2005 | Christopherson |
| 2005/0203546 A1 | 9/2005 | Van Wyk et al. |
| 2005/0256522 A1 | 11/2005 | Francischelli et al. |
| 2006/0030797 A1 | 2/2006 | Zhou et al. |
| 2006/0079829 A1 | 4/2006 | Fulton et al. |
| 2006/0079874 A1 | 4/2006 | Faller et al. |
| 2006/0079877 A1 | 4/2006 | Houser et al. |
| 2006/0079879 A1* | 4/2006 | Faller et al. .................. 606/40 |
| 2006/0253176 A1 | 11/2006 | Caruso et al. |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |

(56) References Cited

U.S. PATENT DOCUMENTS

| | | |
|---|---|---|
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2008/0315829 A1 | 12/2008 | Jones et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0096430 A1 | 4/2009 | Van Der Linde et al. |
| 2009/0105750 A1 | 4/2009 | Price et al. |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0253030 A1 | 10/2009 | Kooij |
| 2009/0264940 A1 | 10/2009 | Beale et al. |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0060231 A1 | 3/2010 | Trainor et al. |
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0058982 A1 | 3/2011 | Kaneko |
| 2011/0074336 A1 | 3/2011 | Miller |
| 2011/0077514 A1 | 3/2011 | Ulric et al. |
| 2011/0080134 A1 | 4/2011 | Miller |
| 2011/0087212 A1 | 4/2011 | Aldridge et al. |
| 2011/0087218 A1 | 4/2011 | Boudreaux et al. |
| 2011/0152901 A1 | 6/2011 | Woodruff et al. |
| 2011/0221398 A1 | 9/2011 | Ferber |
| 2011/0224668 A1 | 9/2011 | Johnson et al. |
| 2011/0247952 A1 | 10/2011 | Hebach et al. |
| 2011/0288573 A1 | 11/2011 | Yates et al. |
| 2012/0179036 A1 | 7/2012 | Patrick et al. |
| 2012/0265230 A1 | 10/2012 | Yates et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |
| 2013/0090552 A1 | 4/2013 | Ramamurthy et al. |
| 2013/0116690 A1 | 5/2013 | Unger |
| 2013/0118733 A1 | 5/2013 | Kumar |
| 2013/0342962 A1 | 12/2013 | Fletcher et al. |
| 2014/0088739 A1 | 3/2014 | Ellis et al. |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | H10-118090 | 5/1998 |
| JP | 2002-186627 | 7/2002 |
| JP | 4602681 | 12/2010 |
| JP | 4836148 | 12/2011 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

U.S. Appl. No. 13/151,481, filed Jun. 2, 2011, Yates et al.
U.S. Appl. No. 13/151,488, filed Jun. 2, 2011, Shelton IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/274,480, filed Oct. 17, 2011, Mumaw et al.

(56) References Cited

OTHER PUBLICATIONS

U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
International Search Report and Written Opinion dated Jul. 6, 2012 for PCT/US2011/059381.
Office Action Non-Final dated Aug. 6, 2013 for U.S. Appl. No. 13/151,471.
Restriction Requirement dated Jul. 5, 2013 for U.S. Appl. No. 13/151,488.
Office Action Non-Final dated Jun. 14, 2013 for U.S. Appl. No. 13/151,498.
Restriction Requirement dated Jun. 24, 2013 for U.S. Appl. No. 13/151,509.
Office Action Final dated Aug. 16, 2013 for U.S. Appl. No. 13/274,516.
Office Action Final dated Sep. 12, 2013 for U.S. Appl. No. 13/274,805.
Office Action Non-Final dated Jun. 14, 2013 for U.S. Appl. No. 13/274,830.
Office Action Final dated Aug. 29, 2013 for U.S. Appl. No. 13/275,563.
Office Action Non-Final dated Aug. 19, 2013 for U.S. Appl. No. 13/276,673.
Office Action Non-Final dated Jun. 12, 2013 for U.S. Appl. No. 13/276,687.
International Search Report dated Jan. 26, 2012 for Application No. PCT/US11/059220.
International Search Report dated Feb. 1, 2012 for Application No. PCT/US11/059223.
International Search Report dated Jan. 12, 2012 for Application No. PCT/US11/059226.
International Search Report dated May 29, 2012 for Application No. PCT/US11/059358.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Mar. 13, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Restriction Requirement dated Feb. 25, 2013 for U.S. Appl. No. 13/274,540.
Office Action Non Final dated Apr. 30, 2013 for U.S. Appl. No. 13/274,540.
Office Action Non-Final dated Apr. 1, 2013 for U.S. Appl. No. 13/274,805.
Restriction Requirement dated Apr. 29, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 6, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
International Search Report and Written Opinion dated Jan. 26, 2012 for Application No. PCT/US2011/059212.
International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
EP Communication dated Feb. 19, 2014 for Application No. EP 11781972.2.
International Preliminary Report on Patentability dated May 7, 2013 for Application No. PCT/US2011/059212.

(56) References Cited

OTHER PUBLICATIONS

International Preliminary Report on Patentability dated May 8, 2013 for Application No. PCT/US2011/059215.
International Preliminary Report on Patentability dated May 7, 2013 for Application No. PCT/US2011/059217.
International Preliminary Report on Patentability dated May 7, 2013 for Application No. PCY/US2011/059218.
International Preliminary Report on Patentability dated May 7, 2013 for Application No. PCT/US2011/059220.
International Preliminary Report on Patentability dated May 7, 2013 for Application No. PCT/US2011/059222.
International Preliminary Report on Patentability dated Feb. 1, 2012 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 8, 2013 for Application No. PCT/US2011/059381.
US Office Action, Non-Final, dated Mar. 28, 2014 for U.S. Appl. No. 13/151,471.
US Office Action, Notice of Allowance, dated Aug. 19, 2014 for U.S. Appl. No. 13/151,471.
US Office Action, Notice of Allowance, dated Nov. 21, 2014 for U.S. Appl. No. 13/151,471.
US Office Action, Non-Final, dated Aug. 14, 2014 for U.S. Appl. No. 13/151,481.
US Office Action, Non-Final, dated Nov. 7, 2014 for U.S. Appl. No. 13/151,488.
US Office Action, Non-Final, dated Mar. 18, 2014 for U.S. Appl. No. 13/151,498.
US Office Action, Notice of Allowance, dated Aug. 6, 2014 for U.S. Appl. No. 13/151,498.
US Office Action, Notice of Allowance, dated Nov. 21, 2014 for U.S. Appl. No. 13/151,498.
US Office Action, Non-Final, dated Jun. 18, 2014 for U.S. Appl. No. 13/151,503.
US Office Action, Non-Final, dated Nov. 6, 2014 for U.S. Appl. No. 13/151,503.
US Office Action, Final, dated Jan. 29, 2014 for U.S. Appl. No. 13/151,509.
US Office Action, Non-Final, dated Jul. 9, 2014 for U.S. Appl. No. 13/151,509.
US Office Action, Notice of Allowance, dated Oct. 28, 2014 for U.S. Appl. No. 13/151,509.
US Office Action, Restriction Requirement, dated Jun. 11, 2014 for U.S. Appl. No. 13/151,512.
US Office Action, Notice of Allowance, dated Oct. 29, 2014 for U.S. Appl. No. 13/151,512.
US Office Action, Restriction Requirement, dated Jul. 11, 2014 for U.S. Appl. No. 13/269,870.
US Office Action, Final, dated Oct. 25, 2013 for U.S. Appl. No. 13/270,667.
US Office Action, Non-Final, dated Jul. 29, 2014 for U.S. Appl. No. 13/270,667.
US Office Action, Restriction Requirement, dated Jul. 9, 2014 for U.S. Appl. No. 13/270,684.
US Office Action, Non-Final, dated Oct. 9, 2014 for U.S. Appl. No. 13/270,684.
US Office Action, Restriction Requirement, dated Sep. 11, 2014 for U.S. Appl. No. 13/270,701.
US Office Action, Non-Final, dated Feb. 14, 2014 for U.S. Appl. No. 13/274,480.
US Office Action, Final, dated Jul. 17, 2014 for U.S. Appl. No. 13/274,480.
US Office Action, Restriction Requirement, dated Dec. 9, 2013 for U.S. Appl. No. 13/274,496.
US Office Action, Non-Final, dated Feb. 6, 2014 for U.S. Appl. No. 13/274,496.
US Office Action, Final, dated May 15, 2014 for U.S. Appl. No. 13/274,496.
US Office Action, Final, dated Aug. 22, 2014 for U.S. Appl. No. 13/274,496.
US Office Action, Restriction Requirement, dated Mar. 28, 2014 for U.S. Appl. No. 13/274,507.
US Office Action, Non-Final, dated Jun. 19, 2014 for U.S. Appl. No. 13/274,507.
US Office Action, Final, dated Jun. 12, 2014 for U.S. Appl. No. 13/274,516.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Non-Final, dated Oct. 22, 2014 for U.S. Appl. No. 13/274,830.
US Office Action, Non-Final, dated Jan. 6, 2014 for U.S. Appl. No. 13/275,514.
US Office Action, Non-Final, dated Sep. 9, 2014 for U.S. Appl. No. 13/275,514.
US Office Action, Final, dated Feb. 28, 2014 for U.S. Appl. No. 13/275,547.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, dated Jul. 9, 2014 for U.S. Appl. No. 13/276,660.
US Office Action, Final, dated Mar. 21, 2014 for U.S. Appl. No. 13/276,673.
US Office Action, Non-Final, dated Aug. 14, 2014 for U.S. Appl. No. 13/276,673.
US Office Action, Notice of Allowance, dated Jun. 2, 2014 for U.S. Appl. No. 13/276,687.
US Office Action, Notice of Allowance, dated Sep. 12, 2014 for U.S. Appl. No. 13/276,687.
US Office Action, Non-Final, dated Aug. 20, 2014 for U.S. Appl. No. 13/276,725.
US Office Action, Non-Final, dated Feb. 28, 2014 for U.S. Appl. No. 13/276,745.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.
Australian First Examination Report dated Jun. 11, 2015 for Application No. AU2011323281.
Chinese First Office Action dated Apr. 16, 2015 for Application No. CN201180063919X.
Chinese First Office Action dated Jun. 1, 2015 for Application No. CN2011800640981.
Japanese Notification of Reasons for Refusal dated Aug. 25, 2015 for Application No. 2013-537831.
US Office Action, Final, dated Apr. 1, 2015 for U.S. Appl. No. 13/151,481.
US Office Action, Notice of Allowance, dated Feb. 25, 2015 for U.S. Appl. No. 13/151,509.

(56) References Cited

OTHER PUBLICATIONS

US Office Action, Notice of Allowance, dated Feb. 17, 2015 for U.S. Appl. No. 13/151,512.
US Office Action, Non-Final, dated Jan. 5, 2015 for U.S. Appl. No. 13/269,870.
US Office Action, Final, dated Aug. 14, 2015 for U.S. Appl. No. 13/269,870.
US Office Action, Notice of Allowance, dated Dec. 17, 2014 for U.S. Appl. No. 13/270,667.
US Office Action, Final, dated Mar. 17, 2015 for U.S. Appl. No. 13/270,684.
US Office Action, Notice of Allowance, dated Jul. 28, 2015 for U.S. Appl. No. 13/270,684.
US Office Action, Non-Final, dated Dec. 16, 2014 for U.S. Appl. No. 13/270,701.
US Office Action, Non-Final, dated Jul. 14, 2015 for U.S. Appl. No. 13/271,364.
US Office Action, Non-Final, dated Apr. 2, 2015 for U.S. Appl. No. 13/274,496.
US Office Action, Non-Final, dated Jul. 22, 2015 for U.S. Appl. No. 13/274,507.
US Office Action, Final, dated May 8, 2015 for U.S. Appl. No. 13/274,516.
US Office Action, Notice of Allowance, dated Sep. 24, 2015 for U.S. Appl. No. 13/274,516.
US Office Action, Notice of Allowance, dated Jan. 21, 2015 for U.S. Appl. No. 13/274,540.
US Office Action, Notice of Allowance, dated Nov. 28, 2014 for U.S. Appl. No. 13/274,805.
US Office Action, Notice of Allowance, dated Jan. 21, 2015 for U.S. Appl. No. 13/274,805.
US Office Action, Notice of Allowance, dated Mar. 23, 2015 for U.S. Appl. No. 13/274,830.
US Office Action, Non-Final, dated Feb. 25, 2015 for U.S. Appl. No. 13/275,495.
US Office Action, Final, dated Mar. 10, 2015 for U.S. Appl. No. 13/275,547.
US Office Action, Final, dated Mar. 13, 2015 for U.S. Appl. No. 13/276,673.
US Office Action, Notice of Allowance, dated Dec. 23, 2014 for U.S. Appl. No. 13/276,687.
US Office Action, Non-Final, dated Jan. 29, 2015 for U.S. Appl. No. 13/276,707.
US Office Action, Notice of Allowance, dated Mar. 13, 2015 for U.S. Appl. No. 13/276,725.
US Office Action, Notice of Allowance, dated Dec. 19, 2014 for U.S. Appl. No. 13/276,745.
US Office Action, Non-Final, dated Dec. 8, 2014 for U.S. Appl. No. 13/277,328.
US Office Action, Final, dated Mar. 24, 2015 for U.S. Appl. No. 13/277,328.
US Office Action, Notice of Allowance, dated Jun. 1, 2015 for U.S. Appl. No. 13/277,328.
Notice of Allowance dated Dec. 6, 2013 for U.S. Appl. No. 13/151,471.
Office Action Final dated Nov. 21, 2013 for U.S. Appl. No. 13/151,498.
Office Action Non-Final dated Sep. 26, 2013 for U.S. Appl. No. 13/151,509.
Office Action Final dated Oct. 25, 2013 for U.S. Appl. No. 13/270,667.
Office Action Non-Final dated Dec. 6, 2013 for U.S. Appl. No. 13/274,516.
Office-Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Notice of Allowance dated Nov. 12, 2013 for U.S. Appl. No. 13/276,687.
Office Action Final dated Sep. 27, 2013 for U.S. Appl. No. 13/276,707.
Office Action Final dated Nov. 8, 2013 for U.S. Appl. No. 13/276,745.
Japanese Office Action, Notification of Reasons for Refusal, dated Sep. 8, 2015 for Application No. 2013-537830.
US Office Action, Notice of Allowance, dated Nov. 30, 2015 for U.S. Appl. No. 13/270,684.
US Office Action, Notice of Allowance, dated Dec. 18, 2015 for U.S. Appl. No. 13/271,364.
US Office Action, Final, dated Dec. 8, 2015 for U.S. Appl. No. 13/274,507.

\* cited by examiner

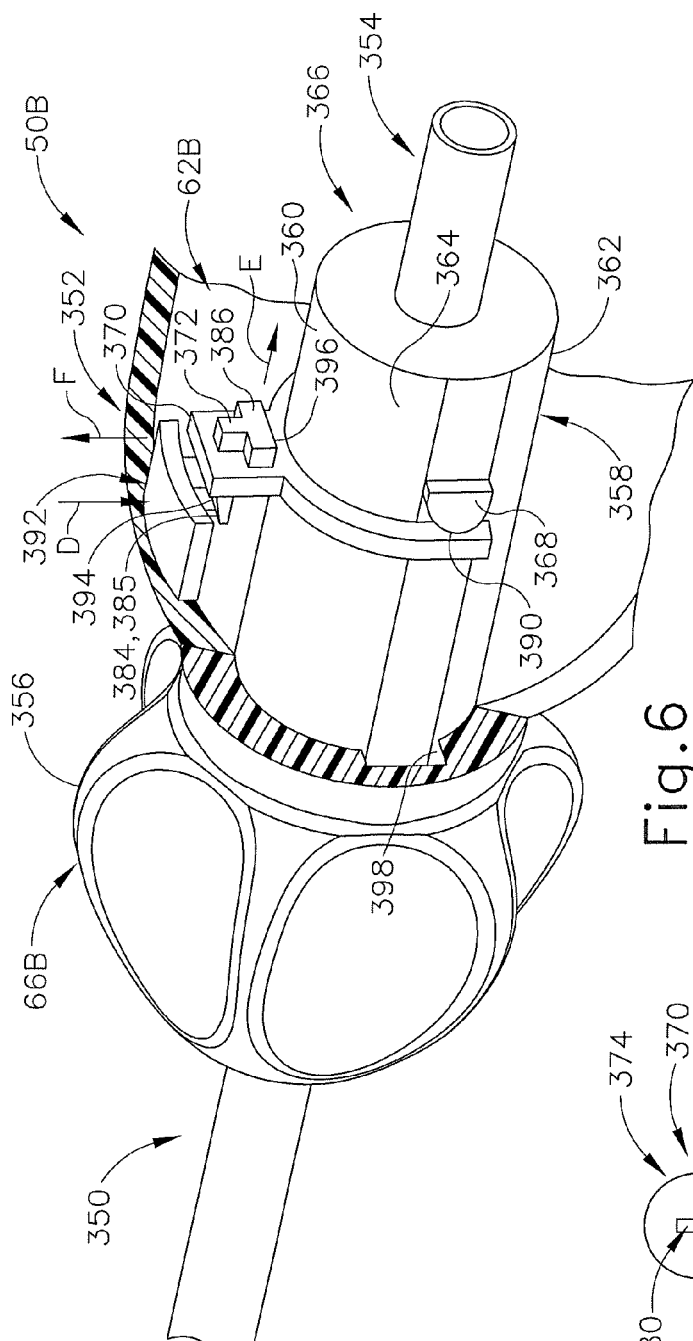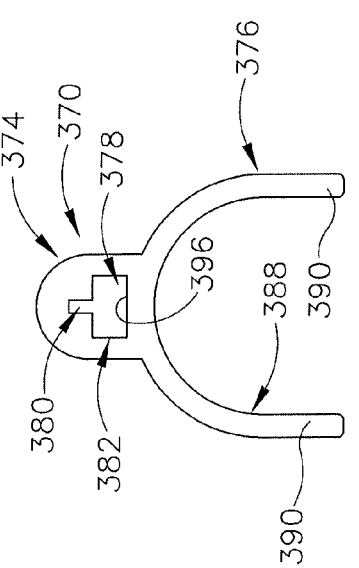

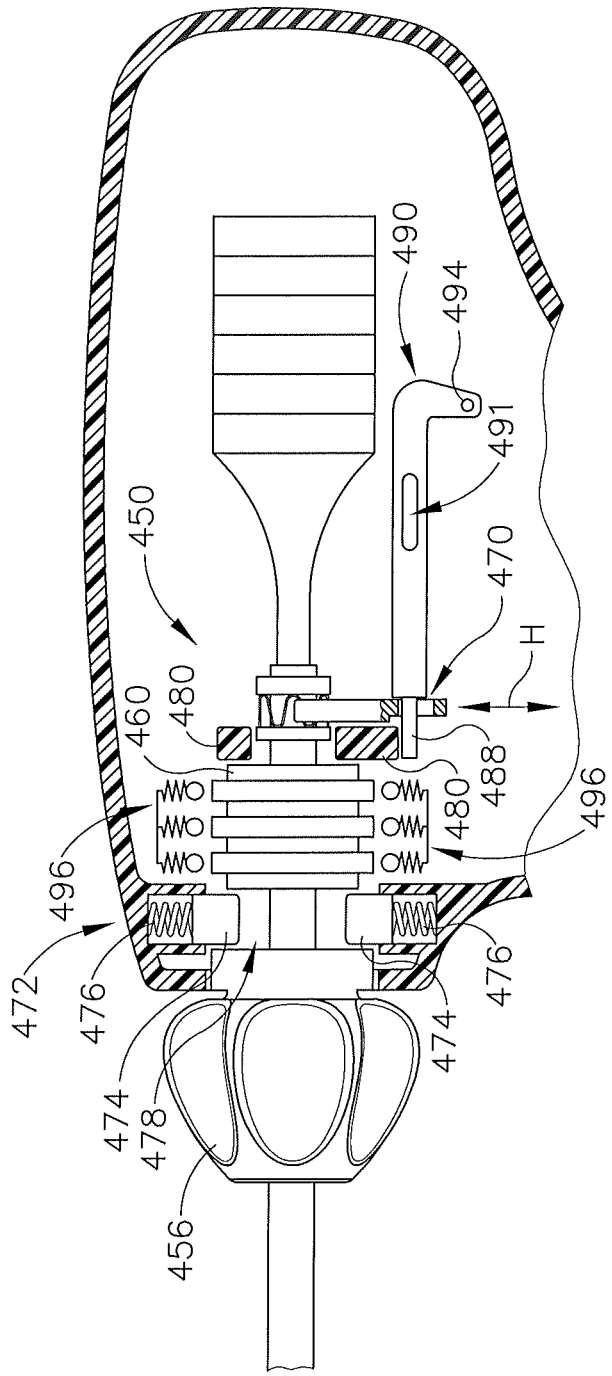
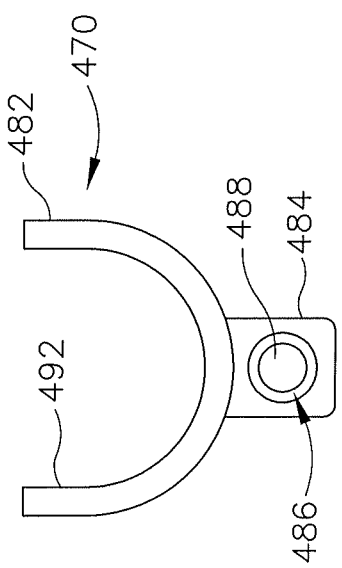
Fig. 10
Fig. 11

SURGICAL INSTRUMENT HANDPIECE WITH RESILIENTLY BIASED COUPLING TO MODULAR SHAFT AND END EFFECTOR

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts a fragmentary, perspective view of an exemplary handle assembly removably connected to an alternate transmission assembly;

FIG. 7 depicts a front elevation view of the exemplary clip component of FIG. 6;

FIG. 10 depicts a fragmentary, elevation view of the exemplary transmission assembly of FIG. 9 inserted into the exemplary surgical instrument of FIG. 9 and an exemplary movable yoke connected to an exemplary inner tube of the exemplary transmission assembly;

FIG. 11 depicts a front elevation view of the exemplary movable yoke of FIG. 10;

Figure 1:
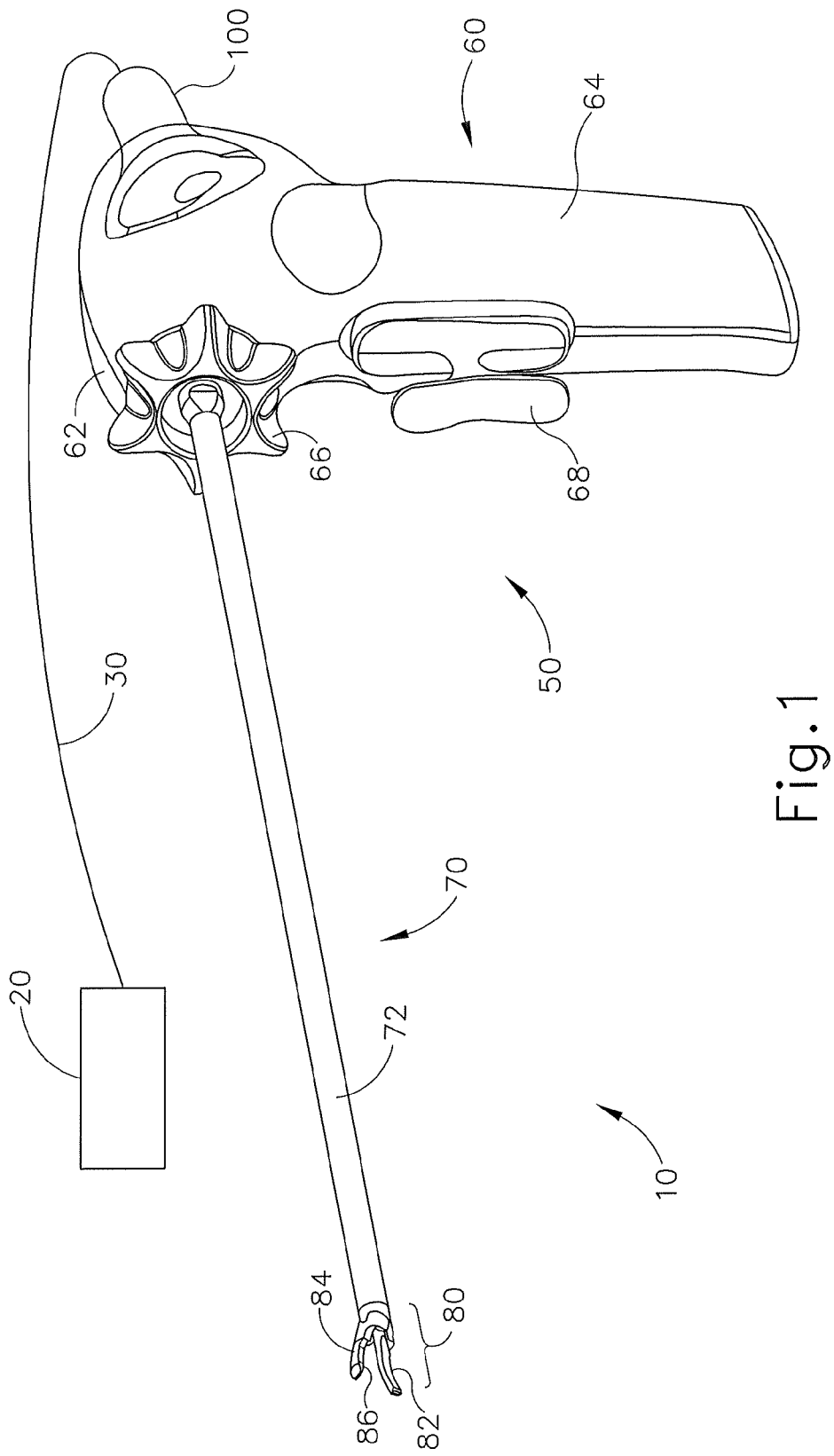
FIG. 1 depicts a perspective view of an exemplary surgical system comprising a surgical instrument and a generator.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Ultrasonic Surgical System

FIG. 1 shows an exemplary ultrasonic surgical system (10) comprising an ultrasonic surgical instrument (50), a generator (20), and a cable (30) coupling generator (20) to surgical instrument (50). In some versions, generator (20) comprises a GEN 300 sold by Ethicon Endo-Surgery, Inc. of Cincinnati, Ohio. By way of example only, generator (20) may be constructed in accordance with the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. While surgical instrument (50) is described herein as an ultrasonic surgical instrument, it should be understood that the teachings herein may be readily applied to a variety of surgical instruments, including but not limited to endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757, the disclosure of which is incorporated by reference herein. For instance, surgical device (50) may include an integral and portable power source such as a battery, etc. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example, transmission assembly (70) is configured as an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, and U.S. Pat. Pub. No. 2008/0200940, entitled "Ultrasonic Device for Cutting and Coagulating," published Aug. 21, 2008, the disclosures of which are incorporated by reference herein. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) that is mechanically and acoustically coupled to the waveguide, a clamp arm (84) operable to pivot at the proximal end of transmission assembly (70), and a clamp pad (86) coupled to clamp arm (84). It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein. Exemplary versions of end effector (80) and transmission assembly (70) will be discussed in greater detail below in reference to the example shown in FIG. 4.

In some versions, transducer (100) comprises a plurality of piezoelectric elements (not shown) that are compressed between first resonator (not shown) and second resonator (not shown) to form a stack of piezoelectric elements. The piezoelectric elements may be fabricated from any suitable material, for example, lead zirconate-titanate, lead meta-niobate, lead titanate, and/or any suitable piezoelectric crystal material, for example. Transducer (100) further comprises electrodes, including at least one positive electrode and at least one negative electrode that are configured to create a voltage potential across the one or more piezoelectric elements, such that the piezoelectric elements convert the electrical power into ultrasonic vibrations. The ultrasonic vibrations are transmitted to blade (82) via the waveguide in transmission assembly (70).

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). A rotation knob (66) is shown in the present example to rotate transmission assembly (70) and transducer (100), but it should be understood that rotation knob (66) is merely optional. Mating housing portion (62) will be discussed in greater detail below in reference to FIG. 2. Lower portion (64) of multi-piece handle assembly (60) shown in FIG. 1 includes a trigger (68) and is configured to be grasped by a user using a single hand. One merely exemplary alternative version for lower portion (64) is depicted in FIG. 1 of U.S. Pat. Pub. No. 2011/0015660, entitled "Rotating Transducer Mount for Ultrasonic Surgical Instruments," published Jan. 20, 2011, now U.S. Pat. No. 8,461,744, the disclosure of which is incorporated by reference herein. Toggle buttons (69), shown in FIG. 2 of the present disclosure, are located on a distal surface of lower portion (64) and are operable to selectively activate transducer (100) at different operational levels using generator (20). For instance, a first toggle button (69) may activate transducer (100) at a maximum energy level while a second toggle button (69) may activate transducer (100) at a minimum, non-zero energy level. Of course, toggle buttons (69) may be configured for energy levels other than a maximum and/or minimum energy level as will be apparent to one of ordinary skill in the art in view of the teachings herein. Moreover, the toggle buttons may be located anywhere else on multi-piece handle assembly (60), on transducer (100), and/or or remote from surgical instrument (50), and any number of toggle buttons may be provided. While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). Such a trigger portion may be operable to activate transducer (100) and may be remote from mating housing portion (62). Multi-piece handle assembly (60) may be constructed from a durable plastic (such as polycarbonate or a liquid crystal polymer), ceramics, metals, and/or any other suitable material as will be apparent to one of ordinary skill in the art in view of the teachings herein. Still other configurations for multi-piece handle assembly (60) will be apparent to those of ordinary skill in the art in view of the teachings herein. For instance, instrument (50) may be operated as part of a robotic system. Other configurations for multi-piece handle assembly (60) will also be apparent to those of ordinary skill in the art in view of the teachings herein. By way of example only, surgical instrument (50) may be constructed in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Coupling Assemblies for Ultrasonic Surgical Instrument

In some instances it may be useful to detach transmission assembly (70) from multi-piece handle assembly (60) and transducer (100). For instance, a detachable transmission assembly (70) may permit the reuse of multi-piece handle assembly (60) with multiple transmission assemblies (70) having various end effectors (80). By way of example only, the various end effectors (80) may have different sized and/or shaped blades (82) or the various end effectors (80) may have entirely different functions, such as RF end effectors, stapling end effectors, cutting end effectors, etc. Furthermore, a single multi-piece handle assembly (60) may be reused for different operations by a user by removing a dirty transmission assembly (70), optionally cleaning multi-piece handle assembly (60), and coupling a new transmission assembly (70) to multi-piece handle assembly (60) for a new operation. Accordingly, configuring multi-piece handle assembly (60) to couple with a variety of transmission assemblies (70) may be preferable for some users of surgical instrument (50).

A. Exemplary Multi-Piece Handle Assembly

Figure 2:
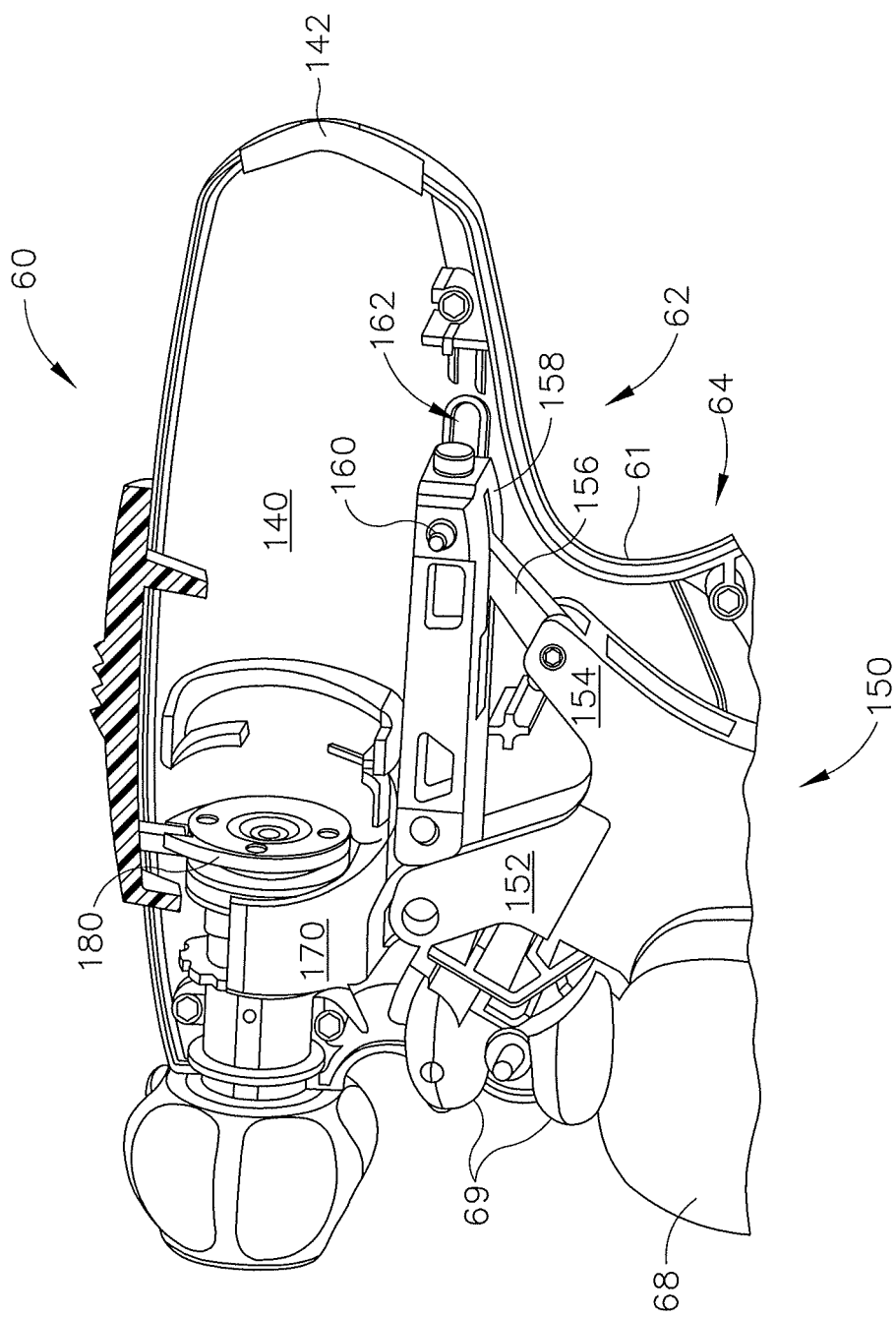
FIG. 2 depicts a partial side elevation view of an exemplary surgical instrument with a portion of a cover removed to show the interior of a mating housing portion of an exemplary multi-piece handle assembly.

FIG. 2 shows a partial side view of multi-piece handle assembly (60) with a portion of a cover (61) removed to show the internal components contained within mating housing portion (62) and a section of lower portion (64). As described above, lower portion (64) includes a pivotable trigger (68) and a pair of toggle buttons (69). Trigger (68) of the present example is pivotable from a distal, open position to a proximal, closed position. A trigger assembly (150) is coupled to trigger (68) and is pivotally supported within multi-piece handle assembly (60). Trigger assembly (150) of the present example comprises a pivotable attachment arm (152) that may be pivoted about a pin (not shown), a trigger arm (154), an intermediate link (156), and an actuation arm (158). Actuation arm (158) is coupled to a trigger yoke (170) at the distal end of actuation arm (158). Actuation arm (158) comprises one or more mounting pins (160) extending outwardly from actuation arm (158) and pins (160) are sized to be slidably received in corresponding elongated channel (162) formed in cover (61). Accordingly, when trigger (68) is pivoted proximally from the open position to the closed position attachment arm (152) and trigger arm (154) pivot within multi-piece handle assembly (60). Intermediate link (156) coupled to trigger arm (154) transfers this pivoting motion from trigger arm (154) to actuation arm (158) to slidably translate actuation arm (158) proximally via pins (160) within channel (162). Trigger yoke (170), which is coupled to actuation arm (158), is translated proximally as well. In the present example, trigger yoke (170) is coupled to a force-limiting mechanism (180), which is further coupled to transmission assembly (70) as will be described in more detail below, to operate inner tubular actuating member (74). A cavity (140), shown in FIG. 2, is configured to receive transducer (100) therein from a transducer aperture (142) formed in cover (61). Cavity (140) is configured to receive at least a portion of transducer (100) therein such that transducer (100) and transmission assembly (70) may be coupled together. Still other configurations for multi-piece handle assembly (60) will be apparent to one of ordinary skill in the art in view of the teachings herein.

B. Exemplary Transducer

Figure 3:
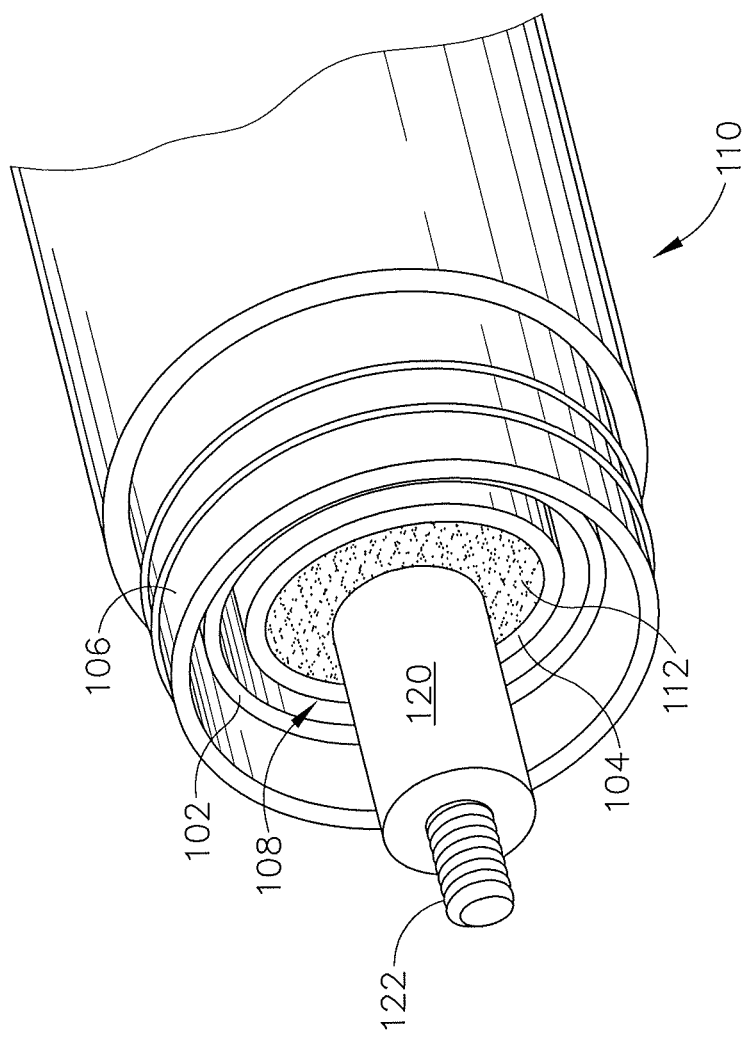
FIG. 3 depicts a partial perspective view of a distal end of an exemplary transducer.

As shown in FIG. 3, transducer (100) of the present example is a tubular component that is coupled to generator (20) via cable (30), though it should be understood that transducer (100) may instead be a cordless transducer. For instance, transducer (100) may instead receive power from a power source that is contained within handle assembly (60), in accordance with the teachings of various references cited herein or otherwise. In the present example, transducer (100) includes a first conductive ring (102) and a second conductive ring (104), which are disposed within a body (110) of transducer (100). In the present example, first conductive ring (102) comprises a ring member having one or more electrical contacts that are disposed on the ring member and that are configured to electrically couple first conductive ring (102) to a power source. First conductive ring (102) is disposed between body (110) and a horn (120) extending distally from body (110). Horn (120) comprises distal horn threads (122) such that horn (120) is coupleable to waveguide (210), as will be discussed below in reference to FIG. 4. First conductive ring (102) of the present example is coaxial with and adjacent to a flange (106). Flange (106) of the present example is configured to further mechanically couple transducer (100) within multi-piece handle assembly (60). A transducer cavity (108) is disposed between first conductive ring (102) and a second conductive ring (104) such that first conductive ring (102) is electrically isolated from second conductive ring (104) and/or other conductive components of transducer (100). First conductive ring (102) is located on a non-conductive platform extending distally from body (110). First conductive ring (102) is electrically coupled to cable (30), shown in FIG. 1, by one or more electrical wires or conductive etchings (not shown) within body (110). Such electrical coupling of first conductive ring (102) to cable (30) may include a slip ring to facilitate free rotation of transducer (100) relative to cable (30).

Second conductive ring (104) of transducer (100) similarly comprises a ring member that is disposed between body (110) and horn (120). Second conductive ring (104) is disposed between first conductive ring (102) and horn (120). As is shown in FIG. 3, first and second conductive rings (102, 104) are coaxial members. Second conductive ring (104) is likewise electrically isolated from first conductive ring (102) and other conductive components of transducer (100). Similar to first conductive ring (102), second conductive ring (104) extends from the non-conductive platform. One or more washer-shaped spacers (112) may be disposed between second conductive ring (104) and horn (120) to isolate the vibrations transmitted through horn (120) from the other components of transducer (100). Second conductive ring (104) is also electrically coupled to cable (30), shown in FIG. 1, by one or more electrical wires or conductive etchings (not shown) within body (110). Such electrical coupling of second conductive ring (104) to cable (30) may also include a slip ring to facilitate free rotation of transducer (100) relative to cable (30). One merely exemplary suitable ultrasonic transducer (100) is Model No. HP054, sold by Ethicon Endo-Surgery, Inc. of Cincinnati, Ohio, though it should be understood that any other suitable transducer may be used.

As shown in the present example, the distal end of transducer (100) threadably couples to the proximal end of a transmission assembly via horn (120). The distal end of transducer (100) also interfaces with one or more electrical connections (not shown) via first and second conductive rings (102, 104) to electrically couple transducer (100) to toggle buttons (69) to provide a user with finger-activated controls for activating transducer (100) while using surgical instrument (50). The interface between the one or more electrical connections and the first and second conductive rings (102, 104) may include a slip ring connection to permit free rotation of transducer (100) relative to multi-piece handle assembly (60). Still other configurations for transducer (100) will be apparent to one of ordinary skill in the art in view of the teachings herein. For instance, first and second conductive rings (102, 104) may be omitted from the distal end of transducer (100) and the electrical coupling of transducer (100) to toggle buttons (69) may be accomplished by alternative structures, such as conductors at the proximal end of transducer (100), conductors located along the side of body (110) of transducer (100), directly from cable (30), and/or otherwise. When transducer (100) of the present example is activated via a toggle button (69), transducer (100) is operable to create mechanical energy in the form of linear oscillations or vibrations, at an ultrasonic frequency (such as 55.5 kHz). When transducer (100) is coupled to transmission assembly (70) via horn (120), these mechanical oscillations are transmitted through the internal waveguide of transmission assembly (70) to end effector (80). In the present example, with blade (82) being coupled to the waveguide, blade (82) thereby oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transmission assembly (70) and transducer (100) have been described, still other suitable configurations for transmission assembly (70) and transducer (100) will be apparent to one of ordinary skill in the art in view of the teachings herein.

C. Exemplary Transmission Assembly for Threaded Attachment

As noted previously, in some instances it may be useful to detach transmission assembly (70) from multi-piece handle assembly (60) and transducer (100). Merely exemplary instances include the use of multi-piece handle assembly (60) with multiple transmission assemblies (70) having different sized and/or shaped blades (82), use with various end effectors (80) with entirely different functions and/or modalities (e.g., RF end effectors, stapling end effectors, cutting end effectors, etc.), or for reuse of a single multi-piece handle assembly (60) for multiple operations by a user. Accordingly, a version permitting the user to swap transmission assemblies (70) with multi-piece handle assembly (60) may be useful.

Figure 4:
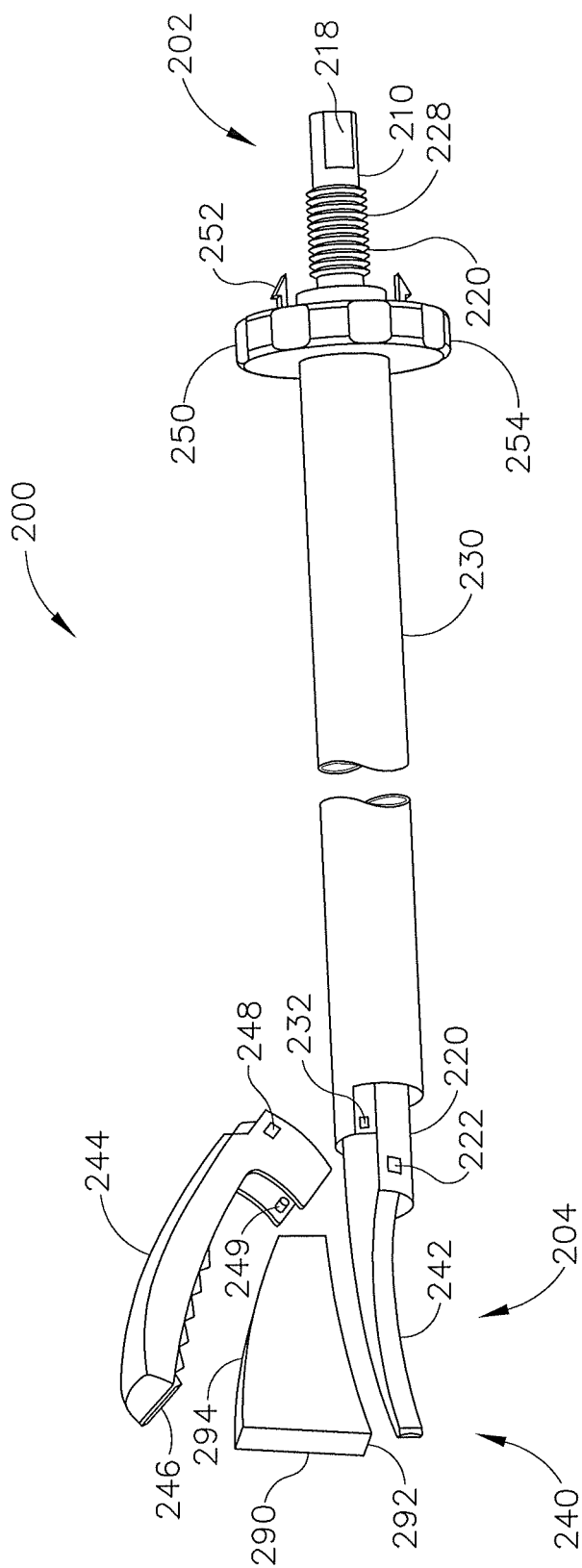
FIG. 4 depicts a perspective view of an exemplary transmission assembly.

One merely exemplary transmission assembly (200) is shown in FIG. 4 having a proximal end (202), a distal end (204), a waveguide (210), an inner tubular actuating member (220), an outer sheath (230), and an end effector (240) at the distal end of transmission assembly (200). In the present example, waveguide (210), inner tubular actuating member (220), and outer sheath (230) are coaxial members with waveguide (230) in the center, inner actuating member (220) disposed about waveguide (210), and outer sheath (230) disposed about inner actuating member (220).

Referring to distal end (204) of transmission assembly (200) first, end effector (240) comprises a blade (242), a clamp arm (244), and one or more optional clamp pads (246). In the present example, blade (242) is coupled to waveguide (210) such that the mechanical vibrations transmitted to waveguide (210) from transducer (100) are also transmitted to blade (242). Merely exemplary couplings for blade (242) to waveguide (210) include welding blade (242) to waveguide (210), integrally forming blade (242) with waveguide (210), mechanically or chemically coupling blade (242) to waveguide (210), and/or any other suitable configuration as will be apparent to one of ordinary skill in the art in view of the teachings herein. In some versions, blade (242) is a curved blade, such as blade (242) shown in FIG. 4; and in some versions blade (242) may be a straight blade. Furthermore, blade (242) may have a variety of shapes and sizes. In the present example, blade (242) is a tapered rectangular blade, though it should be understood that blade (242) may be cylindrical, triangular, hemi-cylindrical, square, hooked, and/or any other shape for blade (242). Furthermore, additional features may be added to blade (242), including spherical tips, hooked tips, square tips, serrated edging, and/or any other additional features. Still other configurations for blade (242) will be apparent to those of ordinary skill in the art in view of the teachings herein.

Clamp arm (244) of the present example is a curved member that corresponds to the curvature of blade (242). Clamp arm (244) may optionally include clamp pads (246) to grip or secure tissue against blade (242). Such clamp pads may be configured in accordance with at least some of the teachings of U.S. Pat. Pub. No. 2006/0079874, entitled "Tissue Pad Use with an Ultrasonic Surgical Instrument," published Apr. 13, 2006. Pivotal movement of clamp arm (244) with respect to blade (242) is accomplished by a first pair of pivot points (248) on clamp arm (244) that pivotally couple to outer sheath (230) and a second set of pivot points (249) on clamp arm (244) that pivotally couple to inner tubular actuating member (220). In the present example, outer sheath (230) is coupleable to multi-piece handle assembly (60) through a rotation knob (250), thereby grounding outer sheath (230). First set of pivot points (248) of clamp arm (244) are pivotally connected to outer sheath (230) via corresponding through holes (232) on outer sheath (230). In some versions, first set of pivot points (248) comprise through holes and a securing pin or rivet may be inserted through first set of pivot points (248) and through through holes (232) to secure clamp arm (244) to outer sheath (230). The pin in this version may be laser welded to clamp arm (244) or the pin may be laser welded to outer sheath (230). Of course through holes (232) may instead be outwardly extending pins and first set of pivot points (248) may be through holes. Still other configurations for first set of pivot points (248) and through holes (232) will be apparent to one of ordinary skill in the art in view of the teachings herein.

Second set of pivot points (249) of clamp arm (244) are pivotally connected to inner tubular actuating member (220) via corresponding through holes (222) on inner tubular actuating member (220). In some versions, second set of pivot points (249) comprise through holes and a securing pin or rivet may be inserted through second set of pivot points (249) and through through holes (222) to secure clamp arm (244) to inner tubular actuating member (220). The pin in this version may be laser welded to clamp arm (244) or the pin may be laser welded to inner tubular actuating member (220). Of course through holes (222) may instead be outwardly extending pins and second set of pivot points (249) may be through holes. Still other pivotable configurations for second set of pivot points (249) and through holes (222) will be apparent to one of ordinary skill in the art in view of the teachings herein.

With clamp arm (244) so secured to outer sheath (230) and inner tubular actuating member (220), clamp arm (244) is pivotable when inner tubular actuating member (220) translates longitudinally. In the present example, inner tubular actuating member (220) is translatable relative to the longitudinal axis of outer sheath (230) and is coupled to force-limiting mechanism (180) within multi-piece handle assembly (60). Thus, when force-limiting mechanism (180) translates via trigger (68) and trigger assembly (150), clamp arm (244) is pivotable from an open position to a closed position. It should be understood that, as with other components referred to herein, clamp arm (84, 244) is merely optional. Likewise, trigger (68) and trigger assembly (150) and the components described herein for pivoting clamp arm (84, 244) are also merely optional. Thus, some versions of end effector (80, 240) may simply consist of a blade (82, 842) and/or other features.

As shown in FIG. 4, a spacer (290) is insertable between clamp arm (244) and blade (242) to maintain clamp arm (244) in the open position. Spacer (290) has a flat bottom surface (292) and an angled top surface (294) in this example. Top surface (294) is set at an angle to maintain clamp arm (244) in the open position relative to blade (242) when bottom surface (292) abuts blade (242). In some versions, bottom surface (292) may be configured to snap or clip onto blade (242) to secure spacer (290) relative to blade (242). Alternatively, a recess may be provided in spacer (290) such that spacer (290) may be slid onto blade (242). Further still, an adhesive may be applied to bottom surface (292) and/or top surface (294) to also secure spacer (290). Thus, when spacer (290) is inserted between clamp arm (244) and blade (242), clamp arm (244) is prevented from pivoting to a closed position. This may permit a user to couple transmission assembly (200) to multi-piece handle assembly (60) while maintaining both clamp arm (244) and trigger (68) in their respective open positions. Alternatively, a user may couple transmission assembly (200) to multi-piece handle assembly (60) without the use of spacer (290). For example, the user may couple different components of transmission assembly (200) with different components of handle assembly (60) at different times, such as in the manner described below or otherwise.

Referring now to distal end (202) of transmission assembly (200), a rotation knob (250) couples outer sheath (230) to multi-piece handle assembly (60). In the present example, rotation knob (250) comprises an inner ring portion (not shown) having one or more connectors (252) extending proximally therefrom, an outer ring (254), and a pin (not shown) extending through outer ring (254), outer sheath (230), inner tubular actuating member (220), and waveguide (210). Accordingly, when outer ring (254) of rotation knob (250) is rotated, waveguide (210), inner tubular actuating member (220), and outer sheath (230) also rotate. Inner ring portion and outer ring (254) of the present example are complementary bearing components such that outer ring (254) is rotatable relative to inner ring portion. It should be understood that the pin does not extend though inner ring portion. As previously noted, inner ring portion includes connectors (252). In the present example connectors (252) are shown as snap-fit connectors, though other suitable connecting features, such as threading, adhesives, pins, clips, snaps, and/or other connectors may be used as will be apparent to one of ordinary skill in the art in view of the teachings herein. When transmission assembly (200) is assembled with multi-piece handle assembly (60) and transducer (100), as will be discussed below, connectors (252) of the present example insert into one or more recesses (not shown) and couple rotation knob (250) to cover (61) of multi-piece handle assembly (60). A release mechanism, such as a push button (not shown) on multi-piece handle assembly (60) or on rotation knob (250) may be provided to decouple connectors (252) from cover (61) when transmission assembly (200) is to be removed. Alternatively, connectors (252) may be designed to break-away when transmission assembly (200) is decoupled. Further still, if threading is used, inner portion of rotation knob (250) may be rotated to decouple from multi-piece handle assembly (60). Still other suitable configurations for rotation knob (250) will be apparent to one of ordinary skill in the art in view of the teachings herein.

Still referring to proximal end (202) of transmission assembly (200), external threads (228) are included at the proximal end of inner tubular actuating member (220) as shown in FIG. 4. External threads (228) screw into complementary threads (not shown) of force-limiting mechanism (180), which is in turn driven by trigger assembly (150). Additionally, a recess having internal threading (218) is included at the proximal end of waveguide (210) as shown in FIG. 4. Internal threading (218) screws onto horn threads (122) to mechanically and acoustically couple waveguide (210) to transducer (100). Of course other suitable configurations for transmission assembly (200) will be apparent to one or ordinary skill in the art in view of the teachings herein. Similarly, various other suitable ways in which transmission assembly (200) may be coupled with handle assembly (60) will be apparent to those of ordinary skill in the art in view of the teachings herein.

III. Exemplary Removable Shaft Connections to Handle Portions

Versions described below relate to connections and uses of disposable rotator and shaft assemblies that are alternative versions of transmission assembly (70) described above. The alternative versions of transmission assembly (70) include one or more resilient members that permit the alternative rotator and shaft assemblies to be selectively coupled with transducer (100), for example, in respective reusable handle portions of ultrasonic surgical instruments. Various exemplary modifications that may be provided for transmission assembly (70) selectively coupleable to multi-piece handle assembly (60) and transducer (100) of instrument (50) will be described in greater detail below. Various suitable ways in which the below teachings may be incorporated into instrument (50) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (50) or devices taught in the references cited herein. The below teachings may be readily applied to various other kinds of instruments, including instruments that would not be classified as ultrasonic surgical instruments. Various other suitable devices and settings in which the below teachings may be applied will be apparent to those of ordinary skill in the art in view of the teachings herein.

A. Exemplary Spring Wire Connection

Figure 5:
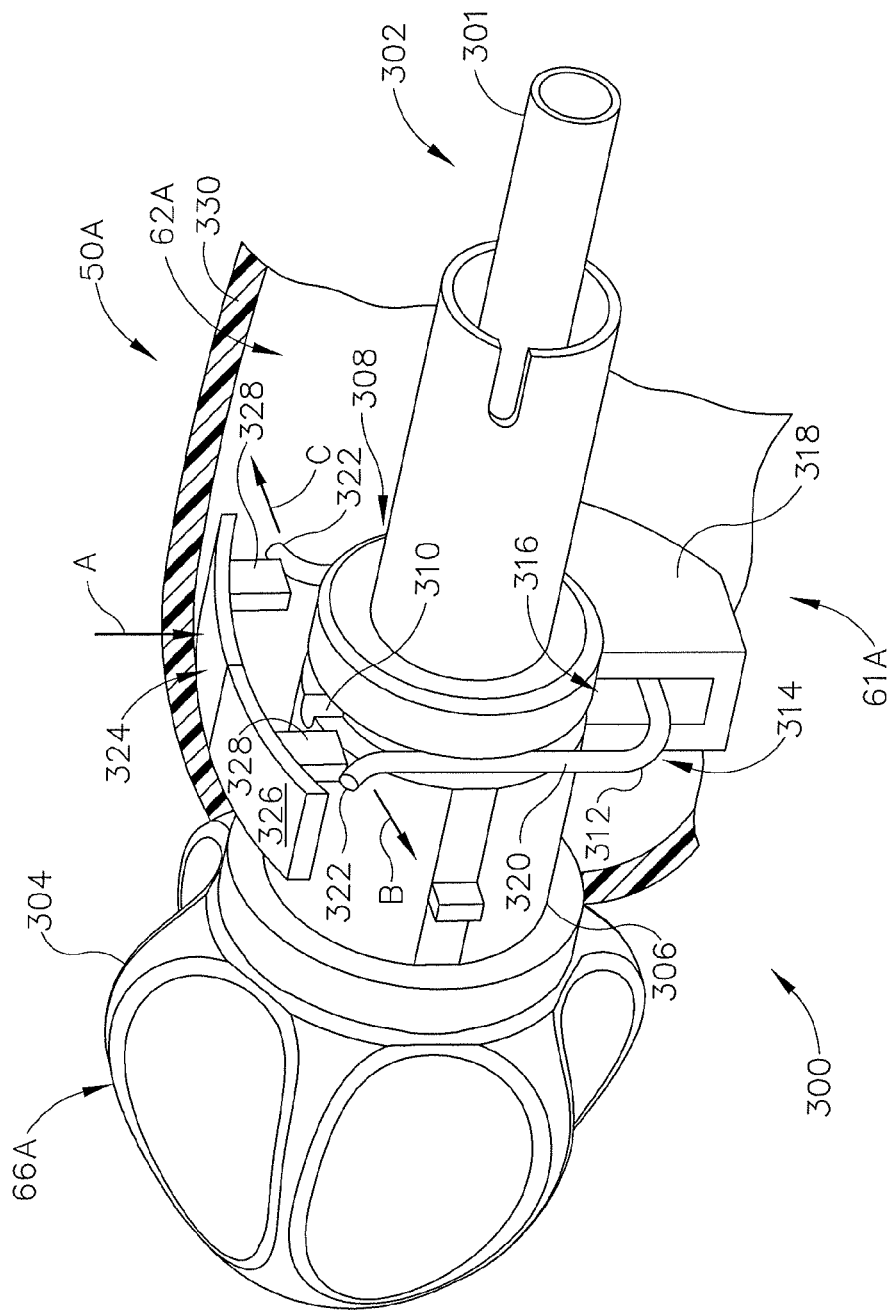
FIG. 5 depicts a fragmentary, perspective view of an exemplary handle assembly removably connected to a transmission assembly.

FIG. 5 shows an exemplary spring wire connection to connect transmission assembly (300) to mating housing portion (62A) of cover (61A) of surgical instrument (50A). Surgical instrument (50A) is similar to surgical instrument (50) described above with the exception of the differences described below regarding the connection and release of the transmission assembly (300) respectively to and from surgical instrument (50A). Transmission assembly (300) includes rotation knob (66A) and shaft (302), which comprises features similar to those described above for transmission assembly (70). Transmission assembly (300), and other alternative versions of transmission assemblies described herein, include distal portions similar to those described above for transmission assembly (70).

Rotation knob (66A) includes knob (304) and cylindrical portion (306) extending proximally from knob (304). Proximal end (308) of cylindrical portion (306) includes an annular groove (310) configured to receive spring wire (312), which generally defines a "U" shape. Proximal end (308) may be tapered to facilitate the engagement of spring wire (312) with rotation knob (66A) as cylindrical portion (306) is inserted proximally into mating housing portion (62A). A curved, intermediate portion (314) of spring wire (312) is received in aperture (316) defined by internal walls (318) at a distal end of mating housing portion (62A). Substantially linear sides (320) extending from intermediate portion (314) are received in groove (310). Opposite, forked ends (322) of spring wire (314) curve in a direction away from intermediate portion (314).

Surgical instrument (50A) includes a button (324). Button (324) includes a top portion (326) from which a pair of prongs (328) project. Each prong (328) abuts an inner surface of a respective forked end (322) of spring wire (312). Prongs (328) and ends (322) are configured and positioned such that prongs (328) cammingly spread ends (322) and sides (320) of spring wire (312) apart when button (324) is pressed downwardly, as described below.

In use, spring wire (312) connects transmission assembly (300) to surgical instrument (50A) when spring wire (312) is received within groove (310). Thus, when button (324) is in an upper position, sides (320) of spring wire (312) remain in groove (310) to couple cylindrical portion (306) to spring wire (312). To disconnect transmission assembly (300) from surgical instrument (50A), a user depresses button (324) in the direction of arrow (A) toward top surface (330) of mating housing portion (62A). This drives sides (320) of spring wire (312) apart and out of groove (310) to fully disengage cylindrical portion (306) from spring wire (312). In particular, as button (324) is depressed, prongs (328) ride down curved inner surfaces of respective forked ends (322) to push forked ends (322) and sides (320) of spring wire (312) away from groove (310) in the respective direction of arrows (B, C), which are generally perpendicular to the direction of arrow (A). As forked ends (322) and sides (320) of spring wire (312) are directed away from groove (310), spring wire (312) disengages from groove (310) of cylindrical portion (306). At this point, transmission assembly (300) may be pulled out and away from mating housing portion (62A).

Notably, to remove transmission assembly (300) from mating housing portion (62A), waveguide (301) may first be unthreaded from the transducer (not shown), as described above with respect to FIGS. 3 and 4. In instances where either the waveguide is not threaded to the transducer to effect a coupling or the transducer is integral with the shaft of the waveguide, transmission assembly (300) may be removed from mating housing portion (62A) in various ways that will be apparent to those of ordinary skill in the art in view of the teachings herein.

B. Exemplary Clip Retention Assembly

In an alternative version, shown in FIG. 6, transmission assembly (350) is connected to mating housing portion (62B) of surgical instrument (50B) via a clip retention assembly (352), described below. Surgical instrument (50B) is similar to surgical instrument (50) described above with the exception of the differences described below regarding the connection and release of the transmission assembly (350) respectively to and from surgical instrument (50B). Transmission assembly (350) includes rotation knob (66B) and shaft (354). Shaft (354) includes features similar to those described above for distal portions of above-described transmission assembly (70).

Rotation knob (66B) includes knob (356) and cylindrical portion (358) extending proximally from knob (356). Cylindrical portion (358) includes top surface (360), bottom surface (362), and side surfaces (364) positioned therebetween. Proximal end (366) of cylindrical portion (358) includes oppositely positioned tabs (368) projecting transversely from side surfaces (364). Retention assembly (352) includes clip (370) and retention component (372). Referring to FIG. 7, clip (370) includes top portion (374) and bottom portion (376). Top portion (374) defines aperture (378) including first space (380) disposed above second space (382), which is wider than first space (380). Bottom portion (376) is U-shaped and is wider than top portion (374). Top portion (374) projects from an upper, central surface of bottom portion (376).

Referring back to FIG. 6, retention component (372) is configured for receipt within top portion (374) and bottom portion (376) of clip (370). When retention component (372) is disposed in clip (370), transmission assembly (350) is connected to mating housing portion (62B), as described below. Retention component (372) includes upper, ramped surface (384) of upper portion (385), which is disposed above lower, box portion (386). Upper portion (385) is configured for receipt within top portion (374) of clip (370), and lower, box portion (386) is configured for receipt within bottom portion (376) of clip (370). When within such a configuration, retention assembly (352) is in a locked configuration, as discussed below.

As shown in FIG. 6, when retention assembly (352) is in the locked configuration, inner edge (388) of clip (370) (shown in FIG. 7) wraps around top surface (360) and side surfaces (365) of cylindrical portion (358). Inner edge (388) is resiliently biased outwardly and is compressed against cylindrical portion (358) when retention assembly (352) is in the locked configuration. Side portions (390) of clip (370) (shown in FIG. 7) abut tabs (368), which provide a stop feature preventing a user from removing transmission assembly (350) from mating housing portion (62B) of surgical instrument (50B). Additionally, in the locked configuration, button (392) is disposed on top surface (392) of mating housing portion (62B) in a first, locked position. Button (392) includes bottom ramped surface (394) that is shaped to abut and rest against ramped surface (384) of retention component (372). Retention component (372) may comprise a retention spring, for example, providing a biasing force against button (392) that may be overcome to compress the spring when button (392) is pressed downwardly. Alternatively, retention component (372) may lack a spring.

After button (392) has been pressed downwardly to move portions of retention component (327) out of aperture (378) of clip (370) as described below, clip (370) will be vertically directed upwards. Without the restriction imposed by retention component (372) acting against bottom inner wall (396) of clip (370) when retention component (372) is fully received in aperture (378), inner edge (388) will naturally bias outwards and away from cylindrical portion (358), allowing clip (370) to ride up side surfaces (365) of cylindrical portion (358). Thus, even if a user releases button (392), and the retention spring releases a biasing force to attempt to return to an original position, the portion of retention component (372) directed away from aperture (378) of clip (370) will now encounter side portions (390) of clip (370) disposed below aperture (378) or a space disposed below and between side portions (390).

In use, to release transmission assembly (350) from mating housing portion (62B) of surgical instrument (50B), a user depresses button (392) downwardly in the direction of arrow (D), which is substantially perpendicular to a longitudinal axis of transmission assembly (350). The force applied to button (392) is transferred from bottom ramped surface (394) to ramped surface (384) of retention component (372) via the abutting interface between the two ramped surfaces (384, 394) to move retention component (372) in the direction of arrow (E) such that box portion (386) of retention component (372) is directed away from aperture (378) of clip (370). Box portion (386) remains disposed above top surface (360) of cylindrical portion (358) when both retained in aperture (378) of clip (370) and after being forced away from aperture (378) of clip (370) in the direction of arrow (E). Button (392) applies force against ramped surface (384) of retention component (372) to move ramped surface (384) in towards aperture (378) of clip (370) while concurrently moving connected box portion (386) out from aperture (378) of clip (370). Button (392) does not apply force against top portion (374) of clip (370) but rather abuts a side face of clip (370) disposed below top portion (374). Clip (370) is upwardly biased but held against cylindrical portion (358) as described above via a downward force applied by box portion (386) against bottom inner wall (396) of clip (370).

After box portion (386) is pushed out of aperture (378), a downwards force is no longer being applied to a bottom inner wall (396) partially defining aperture (378) of clip (370) by box portion (386) to hold clip (370) against cylindrical portion (358) in the locked position described above. Clip (370) will thus vertically move upwards in the direction of arrow (F), which is generally opposite to the downwards direction of arrow (D). As clip (370) moves upwards, side portion (390) will disengage from tabs (368), allowing transmission assembly (350) to be removed or twisted out from mating housing portion (62B) of surgical instrument (50B). Further, in the described unlocked configuration, button (392) is disposed on top surface (392) of mating housing portion (62B) in a second, depressed position.

As shown in FIG. 6, mating housing portion (62B) includes cutouts (398) configured to provide clearance for tabs (368) when transmission assembly (350) is removed from mating housing portion (62B) of surgical instrument (50B).

When transmission assembly (350) is inserted within mating housing portion (62B), the waveguide (not shown) may include a threaded portion that is coupled via a threaded connection to the transducer (not shown), as described above with respect to FIGS. 3 and 4. To remove transmission assembly (350) from mating housing portion (62B), the waveguide (not shown) may thus first be unthreaded from the transducer (not shown), as described above with respect to FIGS. 3 and 4. In instances where either the waveguide is not threaded to the transducer to effect a coupling or the transducer is integral with the shaft of the waveguide, transmission assembly (350) may be removed from mating housing portion (62B) in various ways that will be apparent to those of ordinary skill in the art in view of the teachings herein.

C. Exemplary Latch Arm Connection

Figure 8:
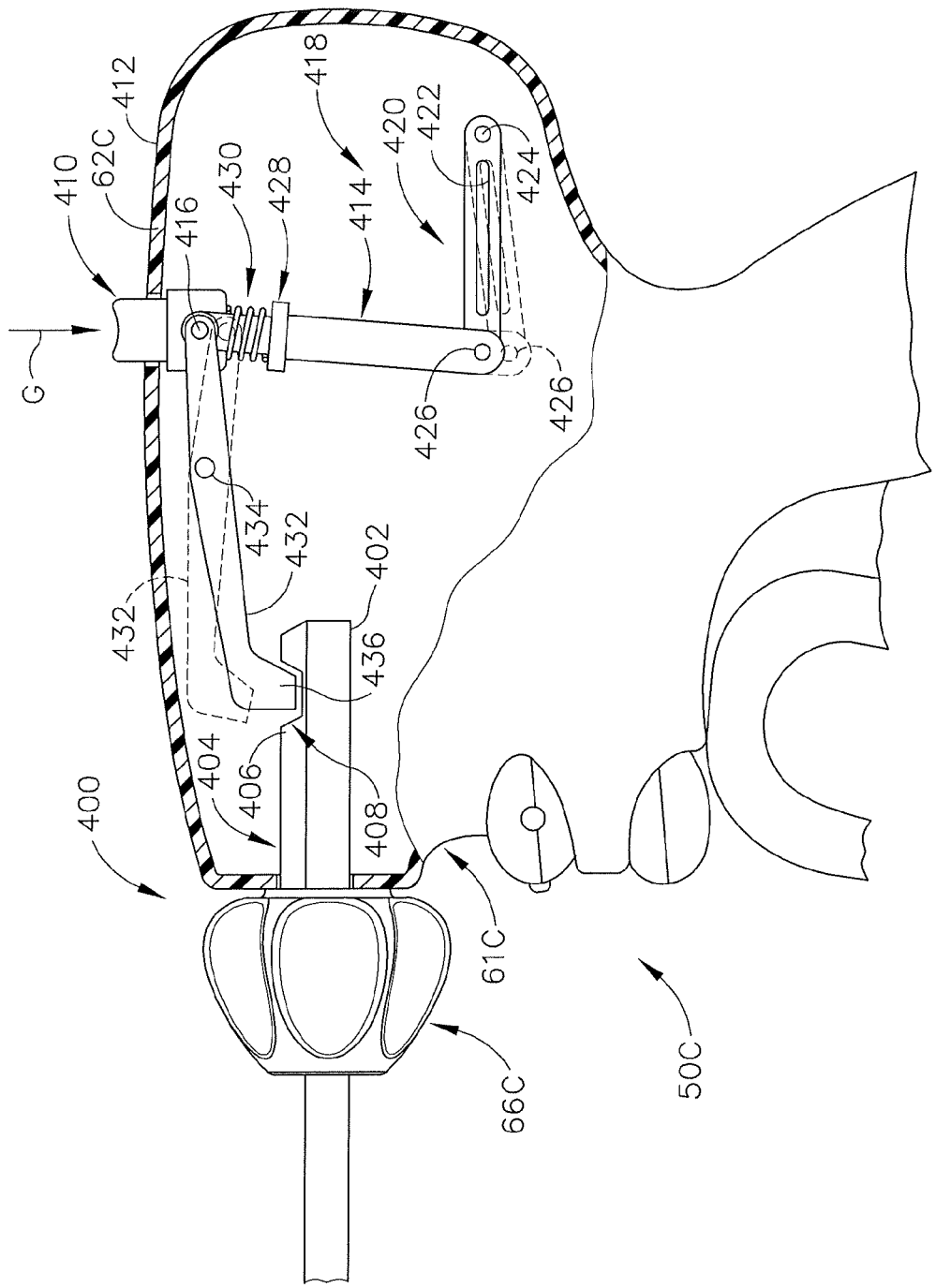
FIG. 8 depicts a side elevation view of an exemplary handle assembly removably connected to another alternate transmission assembly.

In yet another version, shown in FIG. 8, an exemplary latch arm connection connects transmission assembly (400) to mating housing portion (62C) of cover (61C) of surgical instrument (50C). Transmission assembly (400) includes knob (66C) and shaft (402), which includes the features described above for transmission assembly (70). Latch receiving portion (404), which may be a cylindrical portion, extends proximally of knob (66C). Latch receiving portion (404) includes top surface (406) within which lock feature (408) is formed. While lock feature (408) is shown as forming a substantially inverted trapezoidal shape, other shapes such as rectangular, circular, asymmetrical, or symmetrical shapes are possible.

Button (410) is disposed on and within top surface (412) of mating housing portion (62C). Button (410) is connected to lower arm (414) via pin (416). Lower arm (414) is part of movable connector (418). Connector (418) also includes side arm (420) including slot (422), where side arm (420) is fixed to surgical instrument (50C) via fixed pivot (424). Lower arm (414) is pivotally connected to side arm (420) about moving pivot (426). Lower arm (414) includes shroud support feature (428). A biasing member such as a spring (430) is disposed between a lower surface of button (410) and a mating housing portion (62C) of instrument (50C), thereby providing an upward resilient bias to button (410). Spring (430) is wrapped about lower arm (414).

Latch arm (432) is connected to an upper portion of lower yoke arm (414) and button (410) via pin (416). Latch arm (432) includes latch arm pin (434) and distal male locking feature (436).

In a locked position, shown in solid lines and occurring when button (410) is not depressed, spring (430) is in a biased position. The biasing force acts against a lower surface of button (410) to exert a force on distal male locking feature (436) causing feature (436) to mate with female lock feature (408). While features (436, 408) are respectively described as male and female features, the reverse may be possible. The features (436, 408) may slide together or lock together in a snap-fit connection.

To unlock latch arm (432) from latch receiving portion (404) of transmission assembly (400), so that transmission assembly (400) may be removed from mating housing portion (62C), button (410) is downwardly depressed in the direction of arrow (G). The unlocked positions are shown in phantom lines with respect to latch arm (432) and side yoke arm (420). Depressing button (410) moves lower yoke arm (414) downwards and concurrently moves movable pivot (426) downwards, which directs side yoke arm (420) downwards into a more angled position with respect to fixed pivot (424). Side yoke arm (420) may then disengage from an inner tube of shaft (402) to which it was engaged in the locked position. Depressing button (410) additionally compresses spring (430), causing latch arm (432) to rotate about latch arm pin (434) and feature (436) to disengage from feature (408), such that latch arm (432) is no longer locked to transmission assembly (400).

To remove transmission assembly (400) from mating housing portion (62C), the waveguide (not shown) may first be unthreaded from the transducer (not shown), as described above with respect to FIGS. 3 and 4 (as should occur for other versions described herein in which the waveguide is threaded to the transducer). In instances where either the waveguide is not threaded to the transducer to effect a coupling or the transducer is integral with the shaft of the waveguide, transmission assembly (400) may be removed from mating housing portion (62C) in various ways that will be apparent to those of ordinary skill in the art in view of the teachings herein.

In some versions, slot (422) receives a pin that engages a force-limiting mechanism on transmission assembly (400), such as pin (160) (FIG. 2) that engages force-limiting mechanism (180) of transmission assembly (200) described above. Pin (160) is disposed in the proximal portion of slot (422) when assembling or disassembling transmission assembly (400) from mating housing portion (62C). During use of instrument (50C), force-limiting mechanism (180) translates distally via trigger (68) and trigger assembly (150) to effect a closing of clamp arm (244) of the end effector (not shown). During this movement, pin (160) translates distally in slot (422) when side yoke arm (420) is in a substantially horizontal position with respect to transmission assembly (400), which reflects an appropriate motion of travel for pin (160). When pin (160) is disposed in the distal portion of slot (422), a user is prevented from accidently depressing button (410) and releasing transmission assembly (400) from latch arm (432) since pin (160) restricts the downward movement of lower arm (414) and thus prevents the corresponding upward movement of latch arm (432) away from transmission assembly (400). Further, when latch arm (432) is in the release position, shown in phantom in FIG. 8, slot (422) would be angled with respect to the horizontal range of motion for pin (160) and would thus prevent the user from firing the instrument (50C). In effect, pin (160) would remain in the proximal portion of slot (422) and would be prevented from horizontally traveling along its appropriate motion of travel while slot (422) is angled with respect to the horizontal. Thus, force-limiting mechanism (180) would be prevented from distally translating forward as well and would not be able to interact with and close clamp arm (244) of the end effector, as described above.

D. Exemplary Slideable End Effector and Movable Yoke

Figure 9:
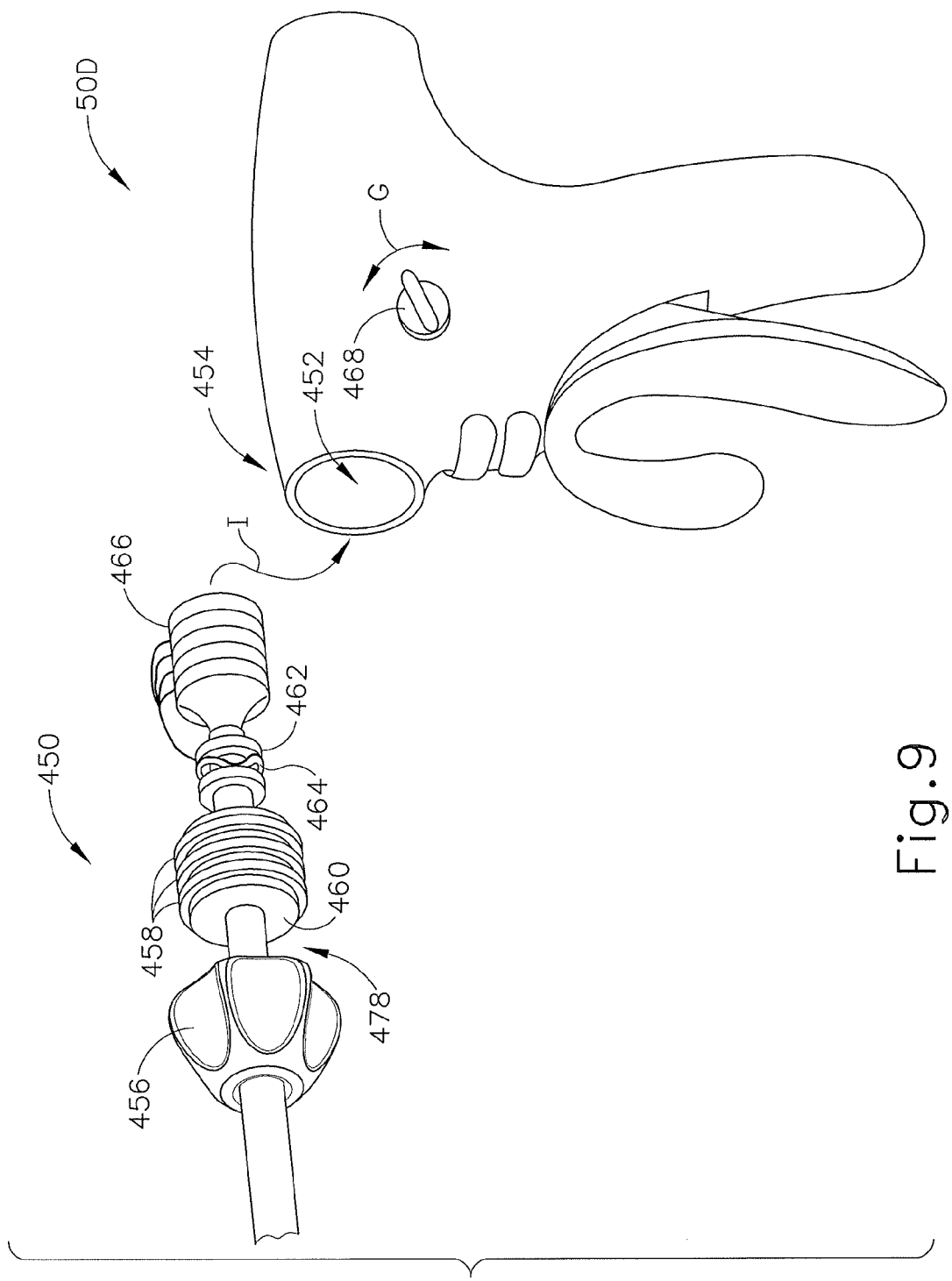
FIG. 9 depicts a perspective view of an exemplary surgical instrument and a fragmentary, side elevation view of an exemplary transmission assembly.

FIGS. 9-11 show a version of an exemplary slideable end effector and movable yoke configuration for surgical instrument (50D). Surgical instrument (50D) includes a transmission assembly (450) that slides into aperture (452) defined at distal end (454) of surgical instrument (50D). Transmission assembly (450) includes rotation knob (456), contact rings (458) about outer tube (460), inner tube (462) with springs (464), a waveguide (not shown) within inner tube (462), and transducer (466) to which the waveguide is connected via, for example, a threaded connection. The tube assembly with respect to outer tube (460), inner tube (462), and the waveguide is similar to that described for transmission assembly (70) above.

As shown in FIG. 9, surgical instrument (50D) includes locking lever (468). When surgical instrument (50D) is in an unlocked position, locking lever (468) is downwardly depressed. When surgical instrument is in a locked position (as shown in FIG. 10), locking lever (468) is upwardly urged. The direction followed with respect to double-headed arrow (G) (FIG. 9) correlates to the direction movable yoke (470) travels with respect to double-headed arrow (H) (FIG. 10), described further below. Various other suitable ways in which lever (468) may be configured for movement will be apparent to those of ordinary skill in the art in view of the teachings herein. Of course, any other suitable components may be used to modify, supplement, and/or substitute lever (468).

When lever (468) is in the unlocked position, transmission assembly (450) is slid into aperture (452) in the direction of arrow (I), and spring loaded lock assembly (472) captures transmission assembly (450) to seat assembly (450) within reusable surgical instrument (50D). As shown in FIG. 10, spring loaded assembly (472) includes rounded protrusions (474) and attached biasing springs (476). When transmission assembly (450) enters aperture (452), transmission assembly (450) initially pushes protrusions (474) against attached springs (476) to move spring loaded assembly (472) out of the way so that transmission assembly (472) may slide into surgical instrument (50D). Groove (478) is formed between rotation knob (456) and outer tube (460). Groove (478) provides a spring loaded lock feature by acting as a female locking feature that receives the male locking feature of protrusions (474), biased into groove (478) via springs (476). Further, a proximal end of outer tube (460) engages stops (480) to prevent transmission assembly (472) from sliding in too far into surgical instrument (50D).

A two-piece yoke (470) rests against a lower stop (480). Yoke (470) is movable in a vertical direction and is controlled by the actuation of lever (468). FIG. 11 shows a front elevation view of yoke (470). Yoke (470) includes an upper U-shaped portion (482) and lower portion (484) disposed below portion (482). Lower portion (484) includes aperture (486) configured for receipt of distal pin (488) of yoke side arm (490). Yoke side arm (490) is pivotally secured to internal walls of surgical instrument (50D) via fixed pivot (494). As shown in FIG. 11, pin (488), is slidably received within aperture (486). Pin (488) has a length sufficient to permit yoke (470) to translate along pin (488), thereby enabling translation of inner tube (462). When lever (468) is in a downward, unlocked position, yoke side arm (490) will be angled with respect to fixed pivot (494) and U-shaped portion (482) will be disengaged from inner tube (462). When lever (468) is in an upward, locked position, an inner surface (492) of U-shaped portion (482) of yoke (470) seats against and engages inner tube (462) in a locked position, as shown in FIG. 10. In particular, U-shaped portion (482) of yoke (470) is positioned between annular flanges of inner tube (462). Additionally or alternatively, yoke (470) may be coupled to a trigger (not shown) to translate yoke (470), which would thereby translate inner tube (462) and effect a pivot of a clamp arm of the end effector at a distal end of transmission assembly (450).

As described above with respect to slot (422) of side yoke arm (420) of instrument (50C) (FIG. 8), yoke side arm (490) of the present example includes a slot (491) configured to receive a translatable pin such as pin (160) (FIG. 2). Slot (491) and a pin of this example operate in a manner similar to slot (422) and pin (160), as described above. The translatable pin is attached to trigger (68) and trigger assembly (150) such that the pin translates when trigger (68) is actuated. In particular, the firing of trigger (68) causes a portion of transmission assembly (450) to translate; while the translatable pin acts in a manner similar to that described above with respect to pin (160) to prevent inadvertent actuation or removal of transmission assembly (450).

Transducer (466) may be configured to rotate within the handpiece of surgical instrument (50D). Electrical power may pass from surgical instrument (50D) to transducer (466) via small spring loaded pin assemblies (496). FIG. 10 shows spring loaded pin assemblies (496) to include contact points that are biased into contact rings (458) via attached springs, which would allow for delivery of electrical power to the transducer, enabling rotation of the entire acoustic/transmission assembly while maintaining electrical continuity between the power source and the transducer. Alternatively, fixed electrical plugs may be used, though rotation might then be precluded.

While the above described interface is described for an ultrasonic surgical instrument (50D), a similar interface could be used for a radio frequency based surgical instrument or powered endocutter instruments, including but not limited to variations of such instruments described in various references cited herein. For example, an RF electrosurgical instrument may include a transmission assembly similar to transmission assembly (450) of instrument (50D) and may use spring contacts such as those of spring loaded pin assemblies (496) to communicate electrical power to an end effector. Also, a surgical stapling instrument such as an endocutter may include a transmission assembly similar to transmission assembly (450) of instrument (50D), though the surgical stapling instrument may not necessarily require spring contacts such as spring loaded pin assemblies (496) for an electrical power (e.g., depending on whether or not the end effector is motorized or otherwise powered). With respect to either an RF electrosurgical instrument or an endocutter, a yoke assembly may be operable to drive a firing beam or knife as through the jaws of an end effector (e.g., to clamp the jaws together and/or to sever tissue clamped between the jaws). Examples of such instruments are described in one or more references cited herein.

E. Exemplary Wave Spring and Yoke Connection

Figure 12:
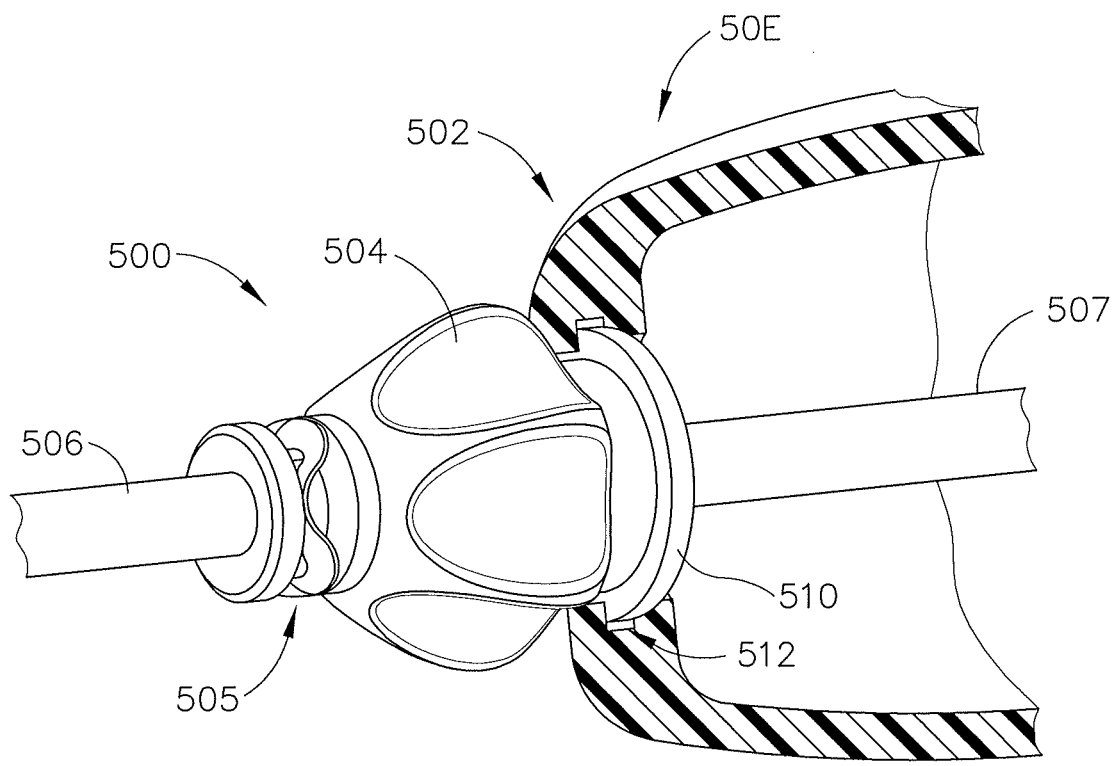
FIG. 12 depicts a fragmentary, perspective view of an exemplary transmission assembly removably connected to a distal aperture of an exemplary surgical instrument via a wave spring component.
Figure 13:
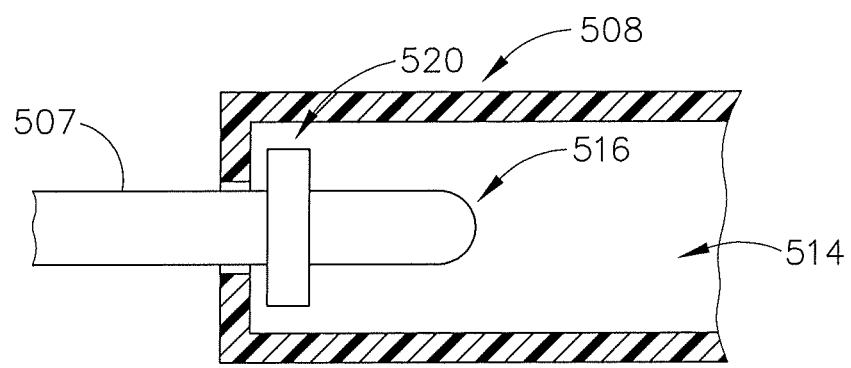
FIG. 13 depicts a fragmentary, elevation view of the shaft of the exemplary transmission assembly of FIG. 12 removably connected to a yoke component of the exemplary surgical instrument.

FIGS. 12 and 13 show a version of connecting transmission assembly (500) to distal end (502) of surgical instrument (50E). Assembly (500) includes rotator or rotation knob (504) and outer sheath (506). Inner tube (507), similar to inner tubular actuating member (220) of transmission assembly (200), translates within outer sheath (506) as described above with respect to inner tubular actuating member (220) and outer sheath (230) of transmission assembly (200). Rotation knob (504) will be spring biased via wave springs (505) relative to surgical instrument (50E) to allow sheath (506) to be in tension with yoke (508). In particular, wave springs (505) bias sheath (506) distally when transmission assembly (500) is coupled with instrument (50E). Rotation knob (504) includes flange (510). Distal end (502) of surgical instrument (50E), and particularly a reusable handle portion of instrument (50E), includes recessed notch (512). Flange (510) is configured to be received within and lock into notch (512) in a mating connection.

FIG. 13 shows a trigger closure yoke (508), which is contained within instrument (50E) and is connected to and actuated by a trigger of surgical instrument (50E) in a manner similar to that described above for earlier versions of instruments. Trigger closure yoke (508) of instrument (50E) includes hollow portion (514) such that flange (520) of inner tube (507) is inserted into yoke (508) from the side through hollow portion (514). Referring back to FIG. 12, wave springs (505) in rotation knob (504) provide sufficient force to remove tolerance between flange (520) of inner tube (507) and trigger closure yoke (508).

To initially attach inner tube (507) to yoke (508), a user slides flange (520) of inner tube (507) along a transverse path into a side opening of yoke (508), shown as hollow portion (514). The user pulls proximally on rotation knob (504) until flange (510) on knob (504) snaps into notch (512) of surgical instrument (50E). Alternatively, flange (520) may be configured to snap into yoke (508) along a longitudinal path and may include resilient portions allowing for flange (520) to enter an aperture at the distal end of yoke (508) in a proximal direction. The resilient portions may be resiliently biased to flare outwardly after entry to abut against walls defining the aperture at the distal end of yoke (508). Such engagement between the resilient portions and the walls at the distal end of yoke (508) may prevent flange (520) from being pulled distally out of yoke (508) after flange (520) is positioned within yoke (508).

In the present example, the snap-fit positioning of knob (504) in notch (512) compresses wave springs (505), such that release of transmission assembly (500) causes springs (505) to pull inner tube (507) into tension with yoke (508) via flange (520), thus removing slop or tolerance from the connection. Waveguide (516) is also coupled with a transducer assembly (not shown). Yoke (508) which is integral with transmission assembly (500) in this example, may also snap into a drive mechanism attached to trigger (68) in a similar manner as to how rotation knob (504) attaches to the reusable handle portion of instrument (50E).

F. Exemplary Mating of Shaft and Transducer

A waveguide may be coupled with a transducer in a non-threaded connection to mate a transmission assembly with a reusable handle. Such an attachment may eliminate a potential need for additional attachment components, such as a torque wrench.

Figure 14:
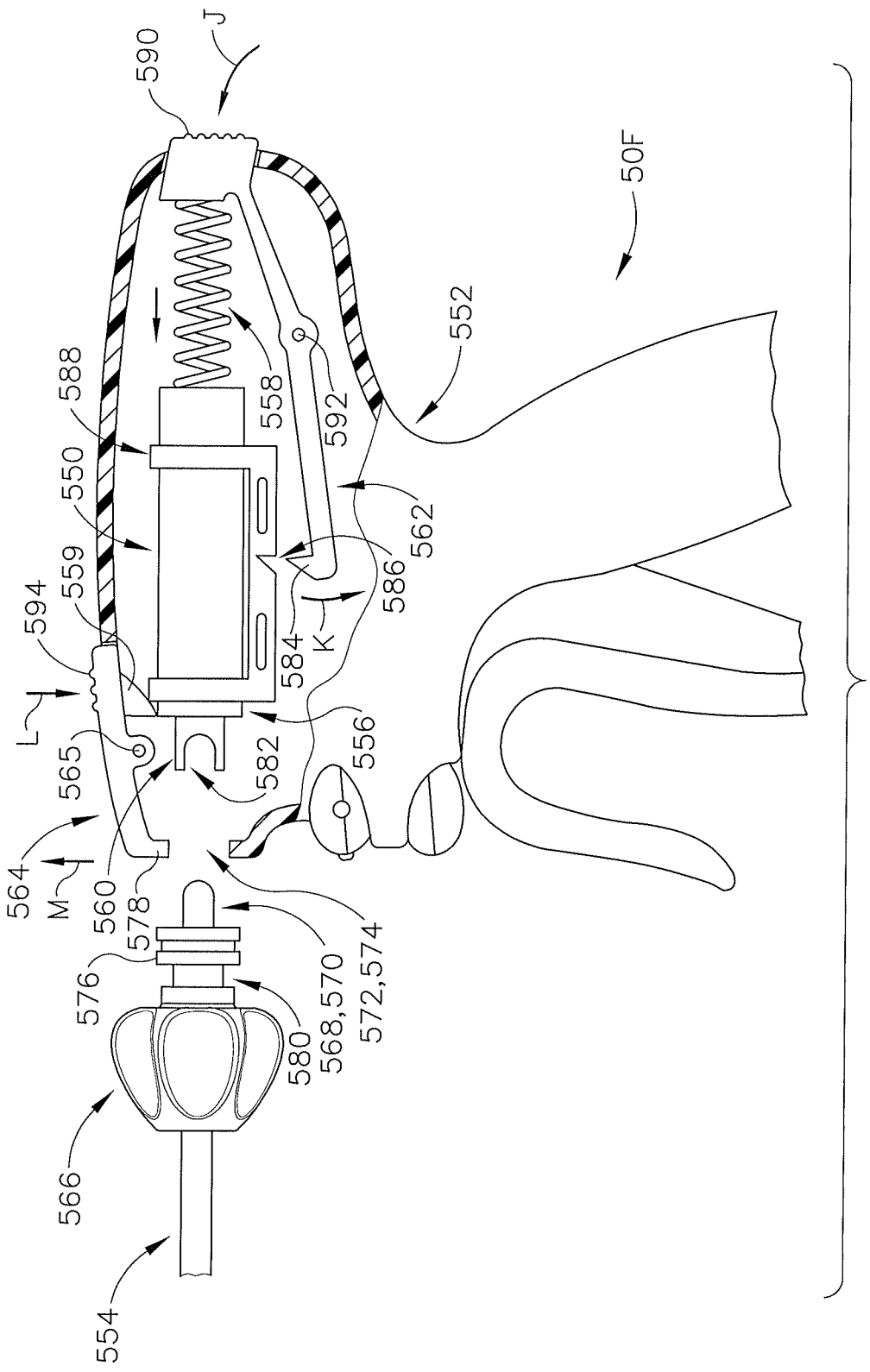
FIG. 14 depicts a side elevation view of another exemplary surgical instrument and exemplary transmission assembly.

FIG. 14 shows ultrasonic surgical instrument (50F) including transducer assembly (550), housing (552), and surgical shaft assembly (554). Transducer assembly (550) includes transducer housing (556), spring (558), and transducer (560). Spring (558) is positioned and configured to bias transducer assembly (550) distally. Spring (558) has a high spring constant or stiffness value to maintain acoustic continuity between transducer assembly (550) and waveguide (568) while transducer assembly (550) is in an active state when waveguide (568) and transducer assembly (550) are coupled together. Housing (552) includes first lever (562) and second lever (564). Shaft assembly (554) includes rotation knob (566) and a male mating feature in the form of waveguide (568).

To install shaft assembly (554) into housing (552) of surgical instrument (50F) and connect assembly (554) to transducer assembly (550), a user pushes proximal end (570) of shaft assembly (554) into aperture (572) at distal end (574) of housing (552). A raised portion (576), which is positioned between rotation knob (566) and proximal end (470) of shaft assembly (554), causes second lever (564) to rotate about pin (565) away from shaft assembly (554) to allow proximal end (570) of shaft assembly (554) to enter aperture (572). After sufficient travel of shaft assembly (554), rotation knob (566) is positioned to allow second lever tab (578) of second lever (564) to latch into groove (580) in knob (566) to lock knob (566) in position.

Additionally, proximal end (570) including a proximal end of waveguide (568) enters distal female end (582) of transducer (560). Up to this point, transducer assembly (550) has been positioned in a retracted position and held in place by first lever tab (584) of first lever (562), which has been in an engaged configuration with notch (586) of transducer retainer (588) of transducer assembly (550).

To firmly couple waveguide (568) with transducer (560), the user presses first lever button (590) in a direction shown by arrow (J). Pressing first lever button (590) rotates first lever tab (584) about pin (592) in the direction of arrow (K) and out of engagement with notch (586) of transducer assembly (550). Previously compressed spring (558) may now partially decompress and resiliently urge transducer (560) into engagement with waveguide (568) via the respective female and male locking features. The biasing force provided by spring (558) is sufficient to maintain acoustic coupling between waveguide (568) and transducer (560), even when transducer (560) is activated.

To remove shaft assembly (554) from instrument (50F), the user depresses second lever button (594) in the direction of arrow (L) to rotate second lever (564) about pin (565) in the direction of arrow (M). This disengages second lever tab (578) from groove (580) of shaft assembly (554), allowing the user to pull shaft assembly (554) out of surgical instrument (50F). The removed shaft assembly (554) may be disposed of and instrument (50F) may be reused with a new shaft assembly.

To reuse instrument (50F), release spring (558) would need to be relocked into its initial compressed position. A user can compress spring (558) by using a camming action with features of transducer (560) and a ring feature (not shown) allowing spring (558) to be compressed. In some versions, transducer (560) is cammed back to a proximal position through the same motion of second lever (564) that is used to release shaft assembly (554). For example, second lever (564) includes a wedge (559) that exerts a proximal camming force on transducer assembly (550), thereby compressing spring (558) when second lever (564) rotates about pin (565) and is disengaged from shaft assembly (554) as described above. This compression of spring (558) may further cause first lever (562) to pivot about pin (592), bringing tab (584) into engagement with notch (586), thereby locking transducer assembly (550) in a proximally retracted position. Thus, releasing shaft assembly (554) from transducer assembly (550) simultaneously cocks or primes transducer assembly (550) for the attachment of another shaft assembly (554). In some other versions, transducer assembly (550) may simply be pushed manually and directly in a proximal direction to compressing spring (558) and re-engage tab (584) with notch (586). Other suitable ways in which transducer assembly (550) and spring (558) may be retracted and cocked will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument comprising:
 (a) a body assembly comprising:
  i. a housing defining a cavity having a distal cavity portion and a proximal cavity portion, wherein the proximal cavity portion is configured to receive an ultrasonic transducer, and
  ii. a resilient member, wherein at least a portion of the resilient member is positioned within the distal cavity portion and is configured to selectively move between an engagement position and a disengagement position; and
 (b) a transmission assembly comprising:
  i. a proximal shaft portion having a proximal end configured to receive the ultrasonic transducer extending proximally therefrom, wherein the proximal shaft portion is configured to be received within the distal cavity portion of the housing,
  ii. a coupling feature disposed at the proximal shaft portion, iii. a distal shaft assembly extending distally relative to the coupling feature, and
iv. an end effector coupled to a distal end of the distal shaft assembly;
wherein the resilient member is configured to selectively engage the coupling feature to mechanically secure at least a part of the transmission assembly to the body assembly in the engagement position, and the resilient member is further configured to selectively disengage from the coupling feature to mechanically release at least the part of the transmission assembly to the body assembly, and
wherein the resilient member in the engagement position extends through the housing and engages the coupling feature such that each of the proximal end of the proximal shaft portion and the proximal cavity portion of the housing remain configured to receive the ultrasonic transducer for operating the surgical instrument.

2. The surgical instrument of claim 1, wherein the body assembly further comprises a user input feature, wherein the resilient member is in communication with the user input feature, and wherein the user input feature is operable to selectively mechanically secure the resilient member to the coupling feature of the transmission assembly.

3. The surgical instrument of claim 1, wherein the transmission assembly further comprises a rotator knob having a proximal portion, wherein the proximal portion of the rotator knob comprises a cylindrical proximal portion.

4. The surgical instrument of claim 1, wherein the coupling feature comprises a recess, and wherein the resilient member of the body assembly comprises a U-shaped spring member, and the U-shaped spring member is configured to be received within the recess.

5. The surgical instrument of claim 4, wherein the U-shaped spring member is defined by a pair of sides connected by an intermediate portion extending therebetween, and wherein the pair of sides are configured to be resiliently spread apart from the engagement to the disengagement positions.

6. The surgical instrument of claim 5, wherein the user input feature is operable to communicate with the pair of sides of the U-shaped spring member, to thereby direct the pair of sides of the U-shaped spring member away from the proximal portion of the rotator knob in the disengagement position.

7. The surgical instrument of claim 6, wherein the recess comprises an annular groove.

8. The surgical instrument of claim 1, further comprising:
(a) the shaft assembly, including:
   (i) an outer sheath;
   (ii) a waveguide extending through the outer sheath and operatively connected to the end effector; and
   (iii) the proximal end including a rotation knob, the rotation knob having a knob and a cylindrical portion extending therefrom, wherein the knob is connected to the outer sheath and the waveguide such that rotating the knob simultaneously rotates the outer sheath and the waveguide relative to the housing, and wherein the cylindrical portion includes the coupling features.

9. A surgical instrument comprising:
(a) a body housing, wherein the body housing has a distal end defining an opening;
(b) a resilient member having a pair of sides connected by an intermediate portion extending therebetween, the pair of sides and the intermediate portion defining a U-shape, wherein the resilient member is configured to selectively move between an engagement position and a disengagement position, wherein the pair of sides are configured to be resiliently spread apart from the engagement position to the disengagement position; and
(c) a shaft assembly, wherein the shaft assembly comprises:
   (i) a distal end, wherein the distal end of the shaft assembly comprises an end effector, and
   (ii) a proximal end, wherein the proximal end of the shaft assembly is sized and configured for insertion in the opening of the distal end of the body housing, wherein the proximal end includes a coupling feature, wherein the pair of sides of the resilient member are configured to selectively retain the shaft assembly relative to the body housing by simultaneously engaging a pair of opposing lateral sides of the coupling feature in the engagement position, and wherein the pair of sides of the resilient member are configured to selectively release the shaft assembly relative to the body housing by simultaneously spreading apart the pair of sides of the resilient member in order to disengage from the pair of opposing lateral sides of the coupling feature in the disengagement position.

10. The surgical instrument of claim 9, further comprising a user input feature, wherein the user input feature is operable to deform the resilient member to spread the pair of sides apart from each other and thereby disengage the resilient member from the two opposing lateral sides of the coupling feature.

11. The surgical instrument of claim 10, wherein the user input feature is operable to deform the pair of sides of the resilient member outwardly from an axis passing through the coupling feature to thereby disengage the pair of sides of the resilient member from the two opposing lateral sides of the coupling feature.

12. The surgical instrument of claim 9, wherein the proximal end of the shaft assembly further comprises a rotation knob, wherein the rotation knob is operable to rotate the shaft assembly relative to the body housing.

13. The surgical instrument of claim 12, further comprising a rotation knob having a knob and a cylindrical portion extending therefrom wherein the coupling feature is located on the cylindrical portion of the rotation knob.

14. The surgical instrument of claim 13, wherein the coupling feature comprises a recess formed in the cylindrical portion of the rotation knob.

* * * * *